US011839651B2

(12) United States Patent
Grassi et al.

(10) Patent No.: US 11,839,651 B2
(45) Date of Patent: Dec. 12, 2023

(54) IMMUNOGENIC COMPOSITIONS AND USES THEREOF

(71) Applicant: INSTITUTE FOR RESEARCH IN BIO-MEDICINE, Bellinzona (CH)

(72) Inventors: Fabio Grassi, Bellinzona (CH); Michele Proietti, Viterbo (IT)

(73) Assignee: INSTITUTE FOR RESEARCH IN BIO-MEDICINE, Bellinzona (CH)

(*) Notice: Subject to any disclaimer, the term of this patent is extended or adjusted under 35 U.S.C. 154(b) by 785 days.

(21) Appl. No.: 16/062,300

(22) PCT Filed: Dec. 21, 2016

(86) PCT No.: PCT/EP2016/082155
§ 371 (c)(1),
(2) Date: Jun. 14, 2018

(87) PCT Pub. No.: WO2017/108935
PCT Pub. Date: Jun. 29, 2017

(65) Prior Publication Data
US 2018/0353600 A1    Dec. 13, 2018

(30) Foreign Application Priority Data
Dec. 21, 2015 (GB) ..................... 1522541

(51) Int. Cl.
| *A61K 39/39* | (2006.01) |
| *A61K 38/53* | (2006.01) |
| *A61P 37/04* | (2006.01) |
| *A61P 31/18* | (2006.01) |
| *A61K 9/51* | (2006.01) |
| *A61K 39/108* | (2006.01) |
| *A61K 39/112* | (2006.01) |
| *A61K 39/00* | (2006.01) |

(52) U.S. Cl.
CPC ............... *A61K 39/39* (2013.01); *A61K 9/51* (2013.01); *A61K 38/53* (2013.01); *A61K 39/0258* (2013.01); *A61K 39/0275* (2013.01); *A61P 31/18* (2018.01); *A61P 37/04* (2018.01); *A61K 2039/55516* (2013.01); *A61K 2039/57* (2013.01); *Y02A 50/30* (2018.01)

(58) Field of Classification Search
CPC .................................................... A61K 39/39
See application file for complete search history.

(56) References Cited

U.S. PATENT DOCUMENTS

| 7,785,618 | B2 * | 8/2010 | Elmaleh | C12N 11/08 |
| | | | | 424/426 |
| 2005/0215505 | A1 * | 9/2005 | Jeong | C12Y 306/01005 |
| | | | | 514/44 R |
| 2009/0297497 | A1 * | 12/2009 | Kishore | A61K 31/7072 |
| | | | | 424/94.61 |
| 2010/0178299 | A1 * | 7/2010 | Sitkovsky | A61K 39/001113 |
| | | | | 424/184.1 |
| 2011/0076258 | A1 | 3/2011 | Grassi et al. | |
| 2012/0282278 | A1 * | 11/2012 | Barden | C07K 16/28 |
| | | | | 424/174.1 |
| 2015/0265685 | A1 * | 9/2015 | Chen | A61K 38/46 |
| | | | | 424/94.6 |
| 2015/0273025 | A1 * | 10/2015 | Xi | A61K 31/795 |
| | | | | 424/78.35 |
| 2017/0347664 | A1 * | 12/2017 | Thompson | C07K 14/32 |

FOREIGN PATENT DOCUMENTS

| CN | 104884069 A | | 9/2015 |
| JP | 2013540698 A | | 11/2013 |
| WO | WO 94/12211 | * | 6/1994 |
| WO | WO 00/23459 | * | 4/2000 |
| WO | 2012-019991 A1 | | 2/2012 |
| WO | 2014-026078 A1 | | 2/2014 |
| WO | WO 2014/026078 A1 | * | 2/2014 |
| WO | WO 2014/052848 A1 | * | 4/2014 |
| WO | 2014/070709 A1 | | 5/2014 |

OTHER PUBLICATIONS

Raffin et al., Expert Opin. Drug Deliv., 2013; 10(5):623-638 (Year: 2013).*
Golkar et al., J Infect Dev Ctries, 2014; 8(2):129-136 (Year: 2014).*
Summers, Annu. Rev. Microbiol., 2001; 55:437-51 (Year: 2001).*
Homayun et al., Pharmaceutics, 2019; 11(129): 1-29 (Year: 2019).*
International Search Report dated Mar. 31, 2017 issued in PCT/EP2016/082155.
Written Opinion dated Mar. 31, 2017 issued in PCT/EP2016/082155.
Proietti, M., et al.. (2014), "ATP-Gated Ionotropic P2X7 Receptor Controls Follicular T Helper Cell Numbers in Peyer's Patches to Promote Host-Microbiota Mutualism", Immunity, 41: 789-801.
Notice of Reasons for Rejection issued in corresponding Japanese Application No. JP 2018-551519 dated Oct. 27, 2020.

* cited by examiner

*Primary Examiner* — Brian Gangle
*Assistant Examiner* — Lakia J Jackson-Tongue
(74) *Attorney, Agent, or Firm* — Harness Dickey & Pierce P.L.C.

(57) ABSTRACT

Compositions capable of enhancing and/or eliciting an immune response in a subject and methods of using the compositions. The compositions are capable of enhancing an IgA immune response and/or an IgG immune response and comprise an agent capable of reducing the level of binding of ATP to a P2X7 receptor to a subject. The compositions are for oral administration.

14 Claims, 23 Drawing Sheets
Specification includes a Sequence Listing.

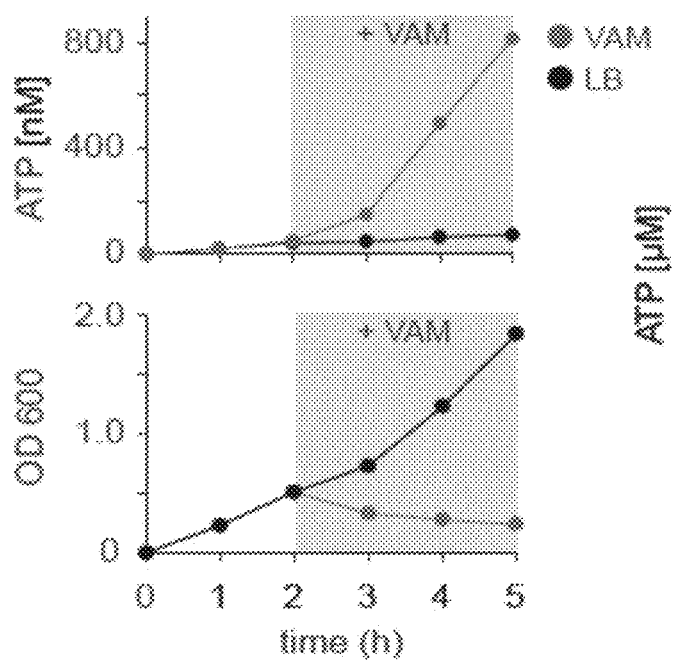
FIG. 1E
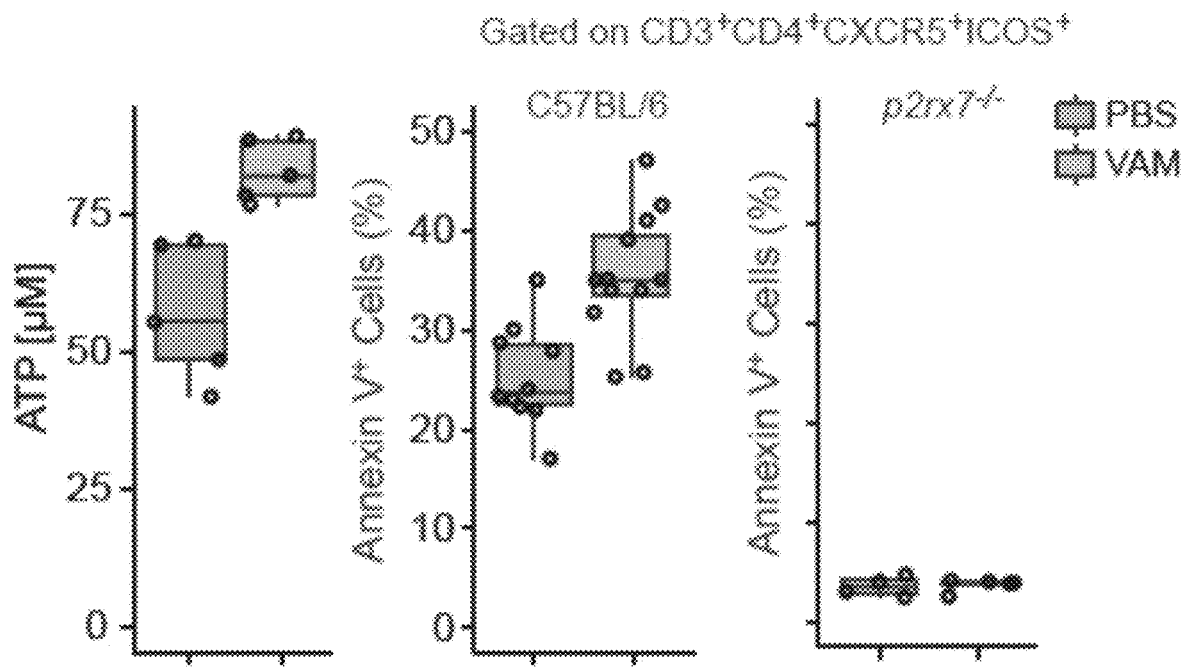
FIG. 1F
FIG. 1G

IMMUNOGENIC COMPOSITIONS AND USES THEREOF

PRIORITY STATEMENT

This patent application is a U.S. national stage filing under 35 U.S.C. § 371 of International Application No. PCT/EP2016/082155 filed 21 Dec. 2016, which claims priority to GB Patent Application No. 1522541.0, filed 21 Dec. 2015. The entire disclosures of each of the above recited applications are incorporated herein by reference.

TECHNICAL FIELD

This invention is in the field of compositions. In particular, the invention relates to immunogenic compositions that may be used as vaccines.

BACKGROUND ART

The gut acts as an entry point for a vast array of foreign antigens in the form of food. The mucosal immune system must ensure that unnecessary immune responses to food antigens are avoided whilst also ensuring that an immune response to any pathogenic organisms is elicited. Furthermore, the gut contains approximately $10^{14}$ commensal microorganisms which live in symbiosis with the host. The mucosal immune system must ensure that an immune response against these organisms is raised in a controlled fashion to allow commensalism. The mucosal immune response must therefore tolerate a large number of non-self antigens, whilst being able to respond to pathogens.

The predominant class of antibody found in the mucosal system is immunoglobulin A (IgA). IgA antibodies secreted in the gut lumen provide mucosal protection by entrapping microorganisms in mucus whilst allowing for commensalism.

The colonised gut is generally insensitive to orally delivered immunogens as vaccines, and therefore inducing a species specific high affinity IgA response using oral vaccination constitutes a major challenge in mucosal immunology. There is therefore a need in the art for particular compositions and immunization protocols which are capable of overcoming the natural refractoriness of the adaptive mucosal system in order to provide high titers IgA (and IgG antibodies) specific to mucosal pathogens.

Only two oral bacterial vaccines have been licensed for use in humans, namely live attenuated *Salmonella typhi* and killed *Vibrio cholerae*.

It is an object of the invention to provide compositions which are capable of eliciting and/or enhancing mucosal immune responses and in particular IgA and IgG immune responses and which can be administered orally.

DISCLOSURE OF THE INVENTION

IgA responses in the gut are controlled by T follicular helper (Tfh) cells which promote maturation of antigen-specific B cells to IgA secreting plasma cells. Tfh cells promote B cell proliferation and facilitate expression of activation-induced deaminase (AID) which promotes Ig class switching and somatic hypermutation. The inventors have previously described that adenosine triphosphate (ATP) gated ionotropic P2X7 receptor has a role in the regulation of Tfh cell abundance[1]. Extracellular ATP was shown to bind to the P2X7 receptor triggering Tfh cell death. Deletion of P2X7 in mice has been shown to result in increased levels of intestinal IgA followed by the depletion of commensals. New data from the inventors show that ATP released by commensals permeates the intestinal epithelium limiting Tfh cell activity.

The inventors have surprisingly found that compositions including an agent which is capable of reducing the level of binding of ATP to a P2X7 receptor are useful for eliciting an effective immune response when administered orally. The compositions may further comprise an immunogen such that an increased IgA and/or IgG immune response is elicited following delivery of the composition, which is specific to the immunogen.

Accordingly, the invention provides a method of enhancing and/or eliciting an immune response in a subject comprising administering a composition capable of enhancing an IgA immune response and/or an IgG immune response comprising an agent capable of reducing the level of binding of ATP to a P2X7 receptor to a subject, wherein the composition is administered to the subject orally.

The invention also provides a composition capable of enhancing an IgA immune response and/or an IgG immune response comprising an agent capable of reducing the level of binding of ATP to a P2X7 receptor for use in enhancing and/or eliciting an immune response in a subject, wherein the composition is for oral administration.

The invention also provides a method of preventing or treating an infectious disease, comprising a method of the invention.

The invention also provides a composition for use according to the invention, for use in preventing or treating an infectious disease.

Compositions of the Invention

The compositions of the invention are capable of enhancing an immune response.

The immune response which the compositions are capable of enhancing may also be elicited by the composition. For instance, in some embodiments, the composition is capable of eliciting an immune response, e.g. where the composition comprises an immunogen. Whereas, in other embodiments the composition is not itself capable of eliciting a specific immune response. For example, the composition may optionally not comprise an immunogen (and therefore not be capable of eliciting an immune response) but may be capable of enhancing an immune response elicited by an immunogen administered separately from the composition of the invention. In this situation, the composition may be combined with a second composition comprising an immunogen prior to use such that the combined compositions are capable of both eliciting and enhancing a specific immune response.

As an alternative, the composition of the invention may be administered to a subject concomitantly or at a similar time to a second composition which is capable of eliciting an immune response, such that the composition of the invention is capable of enhancing the immune response elicited by the second composition.

Where the composition does not comprise an immunogen, it may be administered alone and may be capable of enhancing an immune response elicited by an immunogen already present in the subject.

For example, the composition may be capable of enhancing an immune response against commensals or pathogens already present in the subject to which the composition is to be administered.

The composition may be capable of enhancing and optionally eliciting an IgA immune response and/or an IgG immune response. Preferably, the composition is capable of enhancing and optionally eliciting an IgA immune response.

The composition is preferably for use in enhancing and optionally eliciting a mucosal immune response. The mucosal surfaces of the gastrointestinal, reproductive and respiratory tracts are exposed to the external environment and are therefore highly susceptible to invasion by pathogens. These mucosal surfaces are protected by the elicitation and enhancement of mucosal immune responses. The composition may be for use in enhancing and optionally eliciting an immune response at a gastrointestinal, reproductive or respiratory mucosal surface. Preferably, the composition is for use in enhancing and optionally eliciting an immune response at a gastrointestinal mucosal surface. Such gastrointestinal mucosal surfaces include that of the gut. The gut includes the stomach, the small intestine and the large intestine.

Agents Capable of Reducing the Level of Binding of ATP to a P2X7 Receptor

The compositions of the invention comprise at least one agent capable of reducing the level of binding of ATP to a P2X7 receptor. The composition may comprise multiple agents capable of reducing the level of binding of ATP to a P2X7 receptor. For example, the composition may comprise 2, 3, 4 or more agents capable of reducing the level of binding of ATP to a P2X7 receptor.

These agents are capable of reducing the level of binding of ATP to a P2X7 receptor. Tfh cell death normally occurs following ATP binding to the P2X7 receptor. Therefore reducing the binding of ATP to a P2X7 receptor has the consequence of reducing the triggering of Tfh cell death. Tfh cells support the maturation of B cells to IgA-secreting plasma cells. Therefore, reducing the triggering of Tfh cell death has been shown by the inventors to lead to an increase in B cell maturation and differentiation of B cells to IgA-secreting plasma cells.

The agent capable of reducing the level of binding of ATP to a P2X7 receptor may be in the form of a ligand which is capable of binding to the ATP binding site of the P2X7 receptor. The ligands may competitively bind to the ATP binding site of the P2X7 receptor. Ligands which competitively bind to the ATP binding site of the P2X7 receptor prevent ATP from binding, thereby preventing downstream Tfh cell death. The ligand may be an ATP analogue.

The agent capable of reducing the level of binding of ATP to a P2X7 receptor may be in the form of an antibody which is capable of binding to the P2X7 receptor. The antibody may bind to the ATP binding site of the P2X7 receptor.

The agent capable of reducing the level of binding of ATP to a P2X7 receptor may be in the form of an agent capable of reducing the expression of the P2X7 receptor. The agent may reduce the levels of transcription of a gene encoding the P2X7 receptor. As an alternative, the agent may reduce the levels of translation of an mRNA encoding the P2X7 receptor. As a further alternative, the agent may reduce the levels of pre-mRNA processing of a pre-mRNA encoding the P2X7 receptor. Such agents may take the form of a siRNA or an antisense oligonucleotide.

The agent capable of reducing the level of binding of ATP to a P2X7 receptor may be capable of reducing the concentration of extracellular ATP. In particular, the agent may have ATP-hydrolysing activity. The agent may be an ATP-hydrolysing enzyme.

The agent may be present in the composition as a polypeptide. As an alternative, the agent may be present in the composition as a nucleic acid. Where the agent is present in the composition as a nucleic acid, the nucleic acid may encode a polypeptide.

ATP-Hydrolysing Enzymes

Preferably, the agent capable of reducing the level of binding of ATP to a P2X7 receptor is an ATP-hydrolysing enzyme.

Any ATP-hydrolysing enzyme may be used as an agent capable of reducing the level of binding of ATP to a P2X7 receptor in the compositions of the invention. An ATP-hydrolysing enzyme refers to any enzyme which catalyses the hydrolysis of ATP to ADP, ATP to AMP and/or ADP to AMP. Such enzymes include but are not limited to apyrase, ATPase, ATP-diphosphatase, adenosine diphosphatase, ADPase, ATP diphosphohydrolase and CD39 (Ectonucleoside triphosphate diphosphohydrolase 1, ENTPD1).

Preferably, the ATP-hydrolysing enzyme is apyrase. Where the ATP-hydrolysing enzyme is apyrase, the apyrase may have the sequence of an apyrase from any organism. Preferably, the apyrase is *Shigelli flexneri* apyrase. As an alternative, the apyrase may be *Solanum tuberosum* (potato) apyrase.

Apyrases are nonenergy-coupled NTPases that change the ratios of energy carriers such as ATP, inorganic phosphorus and signalling molecules. Apyrase is found in all eukaryotes in both membrane bound and secreted soluble forms.

The apyrase may be produced by any means. Preferably, the ATP-hydrolysing enzyme is recombinantly produced. Preferably, the ATP-hydrolysing enzyme is recombinantly produced apyrase. Preferably, the apyrase is recombinantly produced apyrase encoded by the sequence provided as GenBank accession no. U04539 (incorporated herein as SEQ ID NO: 1).

As an alternative, the apyrase may be purified directly from its natural source. The apyrase may be purified from a plant source, an animal source or a bacterial source. Preferably, the apyrase is purified from a potato.

Carrier

The agent described above may be present in the composition in a carrier. Any carrier which allows for delivery and/or production of the agent capable of reducing the level of binding of ATP to a P2X7 receptor may be included in the compositions of the present invention.

The carrier may be an expression vector. As an alternative, the carrier may be a cell. The carrier may be a cell which comprises and is capable of expressing an expression vector.

Preferably, the agent is a nucleic acid and is incorporated into an expression vector. Expression vectors which may be used in the compositions of the invention are described below. Expression vectors may be included directly in the composition. As an alternative, the expression vector may be transformed into a host cell which is included in the composition.

Expression Vectors

Expression vectors are capable of enhancing the expression of one or more molecules that have been inserted or cloned into the vector. Examples of such expression vectors include, bacteriophages, autonomously replicating sequences (ARS), centromeres, and other sequences which are able to replicate or be replicated in vitro or in a cell, or to convey a nucleic acid segment to a particular location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids or virus-based vectors such as adenovirus, AAV, lentiviruses.

The expression vector may be a plasmid. Any plasmid expression vector may be used provided that it is replicable and viable in the host.

The expression vector may be mini-circle DNA. Mini-circle DNA are useful for persistently high levels of nucleic acid transcription. The circular vectors are characterized by being devoid of expression-silencing bacterial sequences. For example, mini-circle vectors differ from bacterial plasmid vectors in that they lack an origin of replication, and lack drug selection markers commonly found in bacterial plasmids, e.g. β-lactamase, tet, and the like. Consequently, minicircle DNA becomes smaller in size, allowing more efficient delivery.

The expression vector may be a viral vector.

Any viral vector based on any virus may be used as a carrier for the agent. Commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses).

The viral vector may be an adenoviral (AdV) vector. Adenoviruses are medium-sized double-stranded, non-enveloped DNA viruses with linear genomes that is between 26-48 Kbp. Adenoviruses gain entry to a target cell by receptor-mediated binding and internalization, penetrating the nucleus in both non-dividing and dividing cells. Adenoviruses are heavily reliant on the host cell for survival and replication and are able to replicate in the nucleus of vertebrate cells using the host's replication machinery.

The viral vector may be from the Parvoviridae family. The Parvoviridae is a family of small single-stranded, non-enveloped DNA viruses with genomes approximately 5000 nucleotides long. The viral vector of the disclosure may be an adeno-associated virus (AAV). AAV is a dependent parvovirus that generally requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells. Because progeny virus is not produced from AAV infection in the absence of helper virus, the extent of transduction is restricted only to the initial cells that are infected with the virus. Unlike retrovirus, adenovirus, and herpes simplex virus, AAV appears to lack human pathogenicity and toxicity[2].

Viral vectors based on viruses from the family Retroviridae may be used. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

The viral vector may be a lentivirus vector.

Other viral or non-viral systems known to those skilled in the art may be used as carriers to deliver the agent.

Preferably, the expression vector is a plasmid. As an alternative, preferably the expression vector is a bacteriophage. Where the expression vector is a plasmid or a bacteriophage, the expression vector may be transformed into a bacterial cell and the bacterial cell included in the composition of the invention. The bacterial cell may be *E. coli*. As an alternative the bacterial carrier may be attenuated *Salmonella enterica*. The attenuated *Salmonella enterica* may be of the serovar *Salmonella typhimurium*.

Immunogens

Compositions of the invention may include immunogens capable of inducing a specific immune response. The invention may be used with a wide range of immunogens, for treating or protecting against a wide range of diseases. The immunogen may elicit an immune response that protects against a viral disease (e.g. due to an enveloped or non-enveloped virus), a bacterial disease (e.g. due to a Gram negative or a Gram positive bacterium), a fungal disease, a parasitic disease or any other disease.

The immunogen may take various forms e.g. a whole organism, an outer-membrane vesicle, a protein, a saccharide, a liposaccharide, a conjugate (e.g. of a carrier and a hapten, or of a carrier and a saccharide or liposaccharide), etc.

In a preferred embodiment, the immunogen may take the form of a bacterial carrier which comprises a nucleic acid encoding the agent capable of reducing the binding of ATP to the P2X7 receptor. In this case, the bacterial carrier acts as both the carrier for the agent capable of reducing the level of binding of ATP to P2X7, and as an immunogen. For instance, the composition may comprise a recombinant bacterium such as *Escherichia coli* or attenuated *Salmonella enterica* which comprises a nucleic acid encoding the agent capable of reducing the binding of ATP to the P2X7 receptor. The attenuated *Salmonella enterica* may be of the serovar *Salmonella typhimurium*.

In a particularly preferred embodiment, the immunogen may take the form of a bacterial carrier which comprises a nucleic acid encoding an ATP-hydrolysing enzyme, preferably apyrase. The immunogen may take the form of a bacterial carrier which comprises a nucleic acid encoding *Shigella flexneri* apyrase.

As an alternative, the immunogen may comprise a nucleic acid. The nucleic acid may encode a polypeptide immunogen. The nucleic acid may be present in a carrier as described above. For example, the nucleic acid may be present in an expression vector. Such an expression vector may be present within a cell.

The immunogen and the agent capable of reducing the binding of ATP to the P2X7 receptor may be incorporated into the same expression vector. As an alternative, the immunogen and the agent capable of reducing the binding of ATP to the P2X7 receptor may be incorporated into separate expression vectors. As a further alternative, one of the immunogen and the agent capable of reducing the binding of ATP to the P2X7 receptor may be present in an expression vector whilst the other is not present in an expression vector. For example, the immunogen may be present in an expression vector whilst the agent capable of reducing the binding of ATP to the P2X7 receptor is not. As an alternative, the agent capable of reducing the binding of ATP to the P2X7 receptor may be present in an expression vector whilst the agent capable of reducing the binding of ATP to the P2X7 receptor is not.

The immunogen may not be included in the composition of the invention. As an alternative, an immunogen may be administered separately from the composition of the invention. The composition of the invention may be combined with a second composition comprising the immunogen prior to use, or the composition of the invention may be administered concomitantly with or at a similar time to a second composition comprising an immunogen.

As a further alternative, an immunogen may not be administered in either the composition of the invention or in a second composition. An immunogen may already be present in the subject prior to administration of the composition of the invention.

Specificity of the Immunogen

Preferably, the immunogen elicits an immune response against a gastrointestinal pathogen or a systemic pathogen. Preferably, the systemic pathogen is a mucosally transmitted systemic pathogen.

The immunogen may elicit an immune response against any gastrointestinal bacterial pathogen. Gastrointestinal bacterial pathogens include but are not limited to enterootoxic *Escherichia coli* (ETEC), enteroinvasive *Escherichia coli* (EIEC), verotoxin-producing *Escherichia coli* (EHEC), enteropathogenic *Escherichia coli* (EPEC), *Salmonella* including typhoidal and non-typhoidal *Salmonella*, e.g. *Salmonella typhi, Salmonella enteritidis, Salmonella paratyphi, Salmonella typhimurium,* and *Salmonella choleraesuis, Campylobacter, Vibrio cholera, Shigella boydii, Shigella dysenteriae, Shigella flexneri, Clostridium difficile, Clostridium perfringens, Clostridium botulinum, Bacillus cereus, Vibrio parahaemolyticus, Yersinia enterocoliticia, Helicobacter pylori, Staphylococcus aureus* and *Listeria monocytogenes.*

The immunogen may elicit an immune response against any gastrointestinal viral pathogen. Gastrointestinal viral pathogens include but are not limited to poliovirus, rotavirus, adenoviruses, calciviruses, astroviruses, parvoviruses, coronaviruses, Hepatitis A, D and E, togavirus.

The immunogen may elicit an immune response against any gastrointestinal protozoan pathogen. Gastrointestinal protozoan pathogens include but are not limited to *Giardia lamlia, Cryptosporidium parvum, Isospora belli, Entamoeba histolytica, Entamoeba coli, Endolimax nana, Iodamoeba butschlii, Dientamoeba fraglis, Balantidium coli* and *Trichomonas hominis.*

The immunogen may elicit an immune response against any gastrointestinal helminth pathogen. Gastrointestinal helminth pathogens include but are not limited to *Ascaris lumbricoides, Ancylostoma duodenale, Necator americanus, Strongyloides stercoralis, Taenia saginata, Trichinella spiralis, Capillaria philippinensis, Taenia solium, Diphyllobothrium latum, Hymenolepis nana, Hymenolepis diminuta, Fasciolopsis buski, Metagonimus yokogawi, Heterophyes heterophyes, Gastrodiscoides hominis, Enterobius vermicularis* and *Trichuris trichiura.*

The immunogen may elicit an immune response against any mucosally transmitted systemic pathogen such as human immunodeficiency virus (HIV).

The immunogen may elicit an immune response in any animal. The animal may be a vertebrate or non-vertebrate animal. Vertebrate animals may be mammals. Vertebrate mammals may be human. Examples of mammals include but are not limited to mouse, rat, pig, dog, cat, rabbit, horse, cow, sheep, primate or the like. The animal may be a primate. Preferably the animal is human. The immunogen may elicit an immune response against any pathogen which is capable of infecting the animal. Where an immunogen is used which is capable of eliciting an immune response against a pathogen which is capable of infecting a particular animal or group of animals, the composition comprising the immunogen is suitable for administration to that particular animal or group of animals.

Pharmaceutical Compositions

The compositions disclosed herein may comprise additional components other than the agent and immunogen described above. For example, they typically include one or more pharmaceutically acceptable component. A thorough discussion of such components is available in reference 3.

A composition may include a preservative such as thiomersal or 2-phenoxyethanol.

A composition is preferably sterile. A composition is preferably non-pyrogenic e.g. containing <1 EU (endotoxin unit, a standard measure) per dose, and preferably <0.1 EU per dose. A composition is preferably gluten free.

The compositions of the inventions may be vaccines.

Kits

Also disclosed herein are kits which include a first compartment comprising an agent capable of reducing the level of binding of ATP to a P2X7 receptor.

The kits may further include a second compartment comprising an immunogen.

Methods of Treatment, and Administration of Immunogenic Compositions

Compositions of the invention are intended for administration to animal subjects. As such, the invention provides a method of enhancing and/or eliciting an immune response in a subject, comprising a step of administering a composition of the invention to the subject. The animal subject may be any animal. The animal may be a vertebrate or non-vertebrate animal. Vertebrate animals may be mammals. Vertebrate mammals may be human. Examples of mammals include but are not limited to mouse, rat, pig, dog, cat, rabbit, horse, cow, sheep, primate or the like. The animal may be a primate. Preferably the animal is human. The methods of the invention include methods of preventing or treating an infectious disease in an animal comprising administering a composition of the invention.

The method of enhancing and/or eliciting an immune response in a subject may involve immunizing the subject with a composition of the invention. Accordingly, the invention provides a method of immunizing a subject with a composition comprising an agent capable of reducing the level of binding of ATP to a P2X7 receptor.

The invention also provides use of a composition or kit of the invention as a medicament e.g. for use in enhancing and/or eliciting an immune response in a subject. The invention provides a composition comprising an agent capable of reducing the level of binding of ATP to a P2X7 receptor for use in a method of enhancing and/or eliciting an immune response in a subject. Additionally, the invention provides a composition comprising an agent capable of reducing the level of binding of ATP to a P2X7 receptor for use in preventing or treating an infectious disease. The invention also provides the use of agent capable of reducing the level of binding of ATP to a P2X7 receptor, in the manufacture of a medicament for enhancing an immune response in a subject. Additionally, the invention provides the use of agent capable of reducing the level of binding of ATP to a P2X7 receptor, in the manufacture of a medicament for preventing or treating an infectious disease. The medicament may also comprise an immunogen. As an alternative, the medicament may be for administration in combination with an immunogen.

The invention provides a composition comprising an agent capable of reducing the level of binding of ATP to a P2X7 receptor for use in a method of immunizing a subject. The invention also provides the use of agent capable of reducing the level of binding of ATP to a P2X7 receptor, in the manufacture of a medicament for immunizing a subject. The infectious diseases which may be prevented or treated by the methods and compositions of the invention may be any disease caused by a pathogen. The pathogen may be a gastrointestinal pathogen or a systemic pathogen. The systemic pathogen may be a mucosally transmitted systemic pathogen. The disease may be caused by a bacterial, viral, protozoan or helminth pathogen.

Gastrointestinal bacterial pathogens include but are not limited to enterootoxic *Escherichia coli* (ETEC), enteroinvasive *Escherichia coli* (EIEC), verotoxin-producing *Escherichia coli* (EHEC), enteropathogenic *Escherichia coli* (EPEC), *Salmonella* including typhoidal and non-typhoidal *Salmonella*, e.g. *Salmonella typhi, Salmonella enteritidis, Salmonella paratyphi, Salmonella typhimurium, and Salmonella choleraesuis, Campylobacter, Vibrio cholera, Shigella boydii, Shigella dysenteriae, Shigella flexneri, Clostridium difficile, Clostridium perfringens, Clostridium botulinum, Bacillus cereus, Vibrio parahaemolyticus, Yersinia enterocoliticia, Helicobacter pylori, Staphylococcus aureus* and *Listeria monocytogenes*.

Gastrointestinal viral pathogens include but are not limited to poliovirus, rotavirus, adenoviruses, calciviruses, astroviruses, parvoviruses, coronaviruses, Hepatitis A, D and E, togavirus.

Gastrointestinal protozoan pathogens include but are not limited to *Giardia lamlia, Cryptosporidium parvum, Isospora belli, Entamoeba histolytica, Entamoeba coli, Endolimax nana, Iodamoeba butschlii, Dientamoeba fraglis, Balantidium coli* and *Trichomonas hominis*.

Gastrointestinal helminth pathogens include but are not limited to *Ascaris lumbricoides, Ancylostoma duodenale, Necator americanus, Strongyloides stercoralis, Taenia saginata, Trichinella spiralis, Capillaria philippinensis, Taenia solium, Diphyllobothrium latum, Hymenolepis nana, Hymenolepis diminuta, Fasciolopsis buski, Metagonimus yokogawi, Heterophyes heterophyes, Gastrodiscoides hominis, Enterobius vermicularis* and *Trichuris trichiura*.

Mucosally transmitted systemic pathogens include human immunodeficiency virus (HIV).

The compositions of the invention may be used to prevent or treat enteritis.

The compositions of the inventions may be used as an adjuvant. As an alternative the composition of the invention may be used as a vaccine.

The methods, compositions and uses of the invention will generally be used to generate an antibody response, preferably an IgA immune response and/or an IgG immune response in a subject.

The methods, composition and uses of the invention preferably provide an immunoprotective response, preferably an immunoprotective IgA response in a subject.

The methods, composition and uses of the invention preferably provide an improved immune response compared with the immune response provided by an immunogen in the absence of a composition comprising an agent capable of reducing the level of binding of ATP to a P2X7 receptor. Preferably, the methods, composition and uses of the invention provide an improved IgA immune response compared with the IgA immune response provided by an immunogen in the absence of a composition comprising an agent capable of reducing the level of binding of ATP to a P2X7 receptor Compositions of the invention can be administered in various ways. The usual immunisation route is by oral administration, but other available routes include intranasal, buccal, sublingual etc. Therefore, preferably the composition is formulated for oral administration.

Where the composition is formulated for oral administration the composition may be in the form of tablets, capsules, sachets, dragees, powders, granules, lozenges, powders for reconstitution, liquid preparations, or suppositories.

For oral administration, the compounds of the invention can be provided in the form of tablets or capsules, or as a solution, emulsion, or suspension.

Oral tablets may include a composition according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

Compositions prepared according to the invention may be used as vaccines to treat both children and adults. A subject may be less than 1 year old, 1-5 years old, 5-15 years old, 15-55 years old, or at least 55 years old. Subjects for receiving the vaccines may be elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, people travelling abroad, etc.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve subjects. Multiple doses will typically be administered at least 1 week apart (e.g. about 2 weeks, about 3 weeks, about 4 weeks, about 6 weeks, about 8 weeks, about 12 weeks, about 16 weeks, etc.).

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

BRIEF DESCRIPTION OF THE FIGURES

FIG. 1A-1G Bacterial origin of intestinal ATP. (FIG. 1A) ATP concentration in the lumen of ileum from SPF and germ free mice (GF), bile, urine and serum. (FIG. 1B) ATP concentration in culture medium (bars) and cell growth ($OD_{600}$) of the indicated bacterial species isolated from the small intestine. (FIG. 1C) ATP concentration in serum from (left to right) portal, jugular and inferior caval veins, and heart. (FIG. 1D) FACS analysis of ileal bacteria either untreated (LB) or treated with VAM (VAM) for membrane damage ($DIBAC^+$ cells, upper dot plots), cell death ($Sybr$-$Gren^+DAPI^+$ cells, lower dot plots). (FIG. 1E) ATP concentrations (upper panel) and ileal bacteria growth (lower panel) in untreated (LB) and VAM-treated cultures. (FIG. 1F) Ileal ATP concentrations from mice either gavaged with PBS (left bar) or VAM (right bar). (FIG. 1G) Analysis by FACS of Annexin $V^+$ cells within Tfh cells from PPs of WT and $p2rx7^{-/-}$ mice either untreated (left bar) or orally gavaged with VAM (right bar).

(FIG. 2A, FIG. 2B) Schematic representation of ATP secretion by E. coli (OM, outer membrane, PS, periplasmic space, IM, inner membrane, Cyt, cytosol) (FIG. 2A) and impact of apyrase (FIG. 2B); ATP concentrations (bars) in culture medium and bacterial growth ($OD_{600}$) over time for pBAD28 (FIG. 2A) or pHND10 transformants (FIG. 2B). (FIG. 2C) FACS analysis for anti-E. coli IgA in intestinal wash from mice immunized with pBAD28 or pHND10 transformants. (FIG. 2D, FIG. 2E) Intestinal anti-E. coli IgA quantification in mice immunized with pBAD28 (FIG. 2D) or pHND10 (FIG. 2E) transfected E. coli and tested either with the respective (FIG. 2D) or reciprocal bacterial strain (FIG. 2E). (FIG. 2F) Fold increase of ileal ATP in mice treated with CA (right bars) or PSV (left bars) before and after (12 h) bacterial gavaging. (FIG. 2G) Quantification of anti-E. coli IgA in response to pBAD28 or (FIG. 2H) pHND10 transformants (different γ scale). (FIG. 2I) FACS analysis for IgA in intestinal fluid of mice gavaged with pBAD28 or pHND10 transfected E. coli on the indicated bacterial species.

(FIG. 3A) E. coli staining by IgA in serial dilutions of intestinal washes; (FIG. 3B) the table shows intestinal IgA concentrations and geometric mean of E. coli specific antibodies. (FIG. 3C) Geometric mean of anti-E. coli IgA by FACS plotted against total intestinal IgA concentration and relative function of the fitting curve. (FIG. 3D) Diagram showing time points of E. coli gavaging and ATP measurements in the presence of different antibiotic associations. (FIG. 3E, FIG. 3F) Quantification of anti-E. coli IgA in non-immunized mice (Unim; left bar) or in response to pBAD28 (right bar) and pHND10 (middle bar) transformants in the presence of CA (FIG. 3E) or PSV (FIG. 3F).

(FIG. 10B) Spleen weight in control, untreated mice (left bar), mice immunized with attenuated Salmonella bearing pHND10 and then challenged with virulent Salmonella (middle bar) and mice immunized with attenuated Salmonella bearing pBAD28 and then challenged with virulent Salmonella (right bar). CTRL, untreated mice.

(FIG. 11A) Images of liver tissue in mice immunized with attenuated Salmonella bearing pBAD28 or attenuated salmonella bearing pHND10 and then challenged with virulent Salmonella and of control, untreated mice. (FIG. 11B) Liver histological score in mice immunized with attenuated Salmonella bearing pBAD28 (right bar) or bearing pHND10 (middle bar) and then challenged with virulent Salmonella. The left bar shows liver histological score in control untreated mice.

MODES FOR CARRYING OUT THE INVENTION

Mice and Administration of Antibiotics

Figures 1A, 1B:
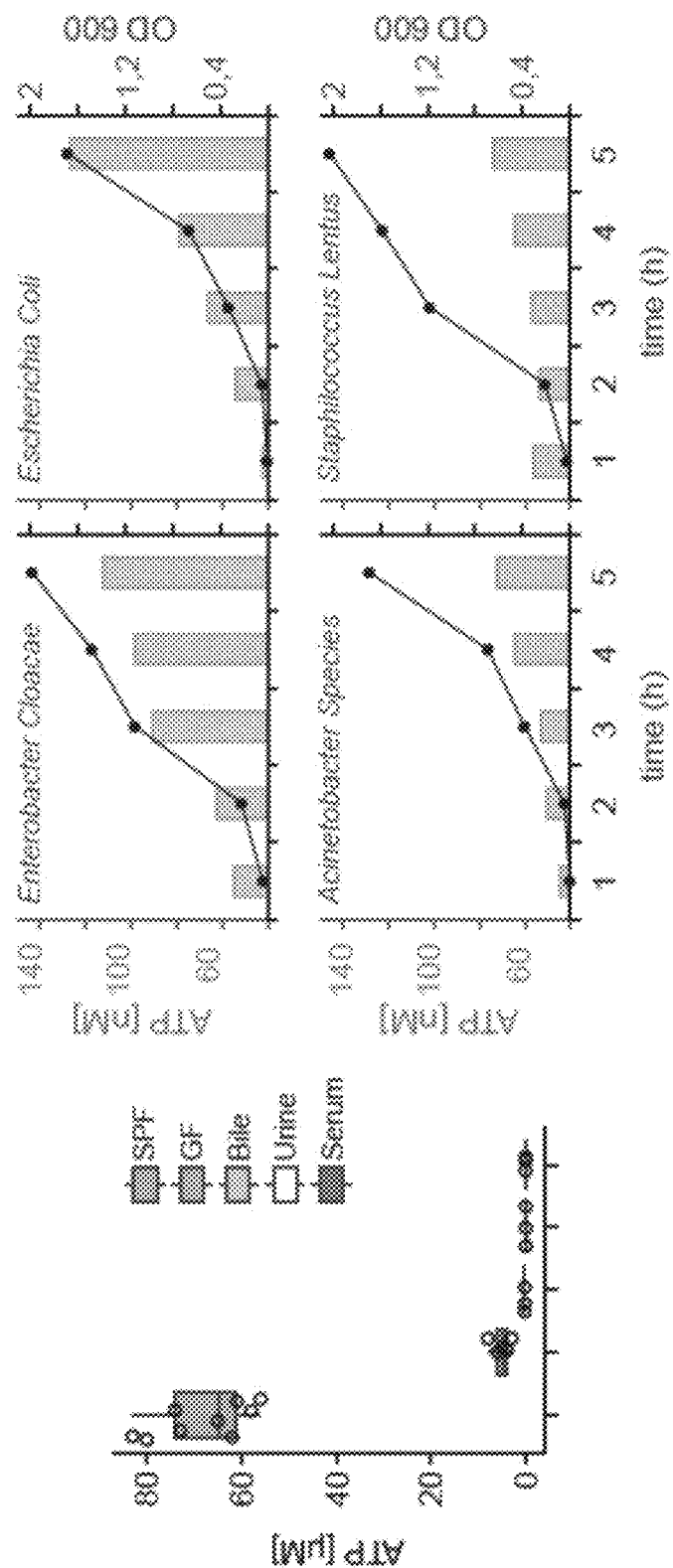

C57BL/6J and p2rx7$^{-/-}$ (B6.129P2-P2rx7tm1Gab/J, Jackson Lab) mice were bred in specific pathogen-free (spf) facility at Institute for Research in Biomedicine, Bellinzona, Switzerland. C57BL/6J germ free mice were maintained in flexible film isolators at the Clean Animal Facility, University of Bern, Switzerland. For antibiotic treatment, mice were given the following antibiotic associations in drinking water for 4 wk: ampicillin 1 g/l and chloramphenicol 0.5 g/l (bactericidal association active on endogenous flora but not pBAD28-transformed *E. coli*) or Stretpomycin 1 g/l, Penicillin 1 g/l and Vancomycin 0.5 g/l (bactericidal on both endogenous and pBAD28-transformed bacteria).

Quantification of ATP

For quantification of ileal ATP, intestinal content was collected by lavage with 10 ml of intestinal wash buffer (PBS, 0.5M EDTA, Soybean trypsin inhibitor, PMSF), spun at 14'000 rpm in a sterile tube, filtered (0.22 µm) to remove any bacteria-sized contaminants and immediately frozen in dry ice. ATP concentration in the intestinal washes was multiplied for the dilution factor to obtain the actual endoluminal ATP concentration. Bile and urine were collected from gallbladder and bladder through puncture with a 34G needle. For quantification of ATP secreted by commensal bacteria in culture, intestinal content was plated on BHI agar and cultured for 16 h at 37° C. Single colonies were picked and cultured in BHI broth. Medium from 16 h cultures of single colonies was centrifuged (15,000×g), the supernatant was collected and filtered (0.22 µm). For quantification of ATP in circulatory districts, inferior caval, jugular and portal veins, and heart were exposed and blood collected through puncture with a 34G needle. Blood was centrifuged at 1000×g and the serum collected and centrifuged a second time at 1000×g. Emolysed sera were discarded. The extracellular ATP concentration was evaluated by bioluminescence assay with recombinant firefly luciferase and its substrate D-luciferin according to the manufacturer's protocol.

Treatment of Bacterial Culture with Antibiotics

Ampicillin (2.5 µg/ml), vancomycin (1 µg/ml), metronidazole (1 µg/ml) were added to intestinal bacterial culture at 0.5 OD. Supernatants from bacterial cultures were collected 3, 4 and 5 h after addition of antibiotics, spun at 14'000 rpm in a sterile tube and filtered (0.22 µm). ATP concentration was evaluated by bioluminescence assay (see above).

Antibodies and Flow Cytometry

The following mAbs were purchased from BD Biosciences: biotin conjugated anti-CXCR5 (clone: 2G8, Cat.#: 551960) and phycoerythrin (PE) conjugated anti-ICOS (clone: 7E.17G9, Cat.#: 552146). PE-Cy7 conjugated anti-CD4 (Clone:GK1.5, Cat.# 100422) and APC conjugated streptavidin (Cat.#: 405207) were from Biolegend. Percp-eFluor710 conjugated anti-CD3 (Clone: 17A2, Cat.#: 46-0032-80) was obtained from eBioscience. Annexin V staining was performed in Biolegend Annexin V binding buffer (Cat.#422201) (1×10$^6$ cells/ml) following the manufacturer's protocol. Data were analysed using FlowJo software (TreeStar, Ashland, Oreg.) or FACS Diva software (BD Biosciences).

Plasmids

Full length phoN2::HA fusion of *S. flexneri* was cloned into the polylinker site of plasmid pBAD28 (ATCC 8739387402), under the control of the $P_{BAD}$ L-arabinose inducible promoter, generating plasmid pHND10 (ref. 8).

Oral Immunization with *E. coli* and Flow Cytometry for Detection of Anti-*E. coli* IgA

*E. coli* transformed with pBAD28 or pHND10 were aseptically inoculated into LB medium containing arabinose (0.3%) and ampicillin (100 µg/ml), and incubated at 37° C. for 18 h. Bacteria were harvested by centrifugation, washed in sterile PBS and concentrated to a density of 2×10$^{10}$ CFUs/ml in PBS. Bacterial suspensions (10$^{10}$ CFUs in 300 µl) were gavaged into the stomach. The procedure was repeated every 3 day for 3 weeks and mice were sacrificed at day 28. Intestinal contents were collected by lavages with 5 ml of intestinal wash buffer (PBS, 0.5M EDTA, Soybean trypsin inhibitor, PMSF), spun at 14'000 rpm in a sterile tube and filtered (0.22 µm) to remove any bacteria-sized contaminants[4]. For flow cytometry analysis of anti-*E. coli* IgA, 3 ml of LB broth were inoculated with single colonies and cultured overnight at 37° C. Cultures were subsequently centrifuged (3 min at 7000 rpm), washed 3 times with sterile-filtered PBS, 2% BSA, 0.005% NaN$_3$ and resuspended at a density of approximately 10$^7$ bacteria per ml. Intestinal contents and bacteria were then mixed and incubated at 4° C. for 1 h. Bacteria were washed twice, before being resuspended in monoclonal FITC-anti-mouse IgA (Southern Biotech, Cat.#: 1040-02, working dilution 1:200). After 1 h incubation bacteria were washed twice and resuspended in 2% paraformaldehyde in PBS for acquisition on a FACSCanto using FSC and SSC parameters in logarithmic mode. For each animal analyzed, ELISA was used to determine the total IgA concentration in an undiluted aliquot of the same intestinal wash sample used for surface staining of *E. coli*. This value was used to calculate the total IgA concentration at each dilution of intestinal wash used for flow cytometry of *E. coli* and was plotted against the geometric mean fluorescence obtained in flow cytometry.

Oral Immunization with Attenuated *Salmonella typhimurium* and Flow Cytometry for Detection of Anti-*Salmonella typhimurium* IgA Avirulent gyrA1816 Δcya1 Δcrp1 *S. typhimurium* (which have mutations in cya and crp genes and are incapable of producing functional adenylate cyclase as well as cyclic AMP receptor protein) (ATCC® 53648™) transformed with pBAD28 or pHND10 were aseptically inoculated into LB medium containing arabinose (0.05%) and chloramphenicol (30 µg/ml), and incubated at 37° C. for 18 hours. Bacteria were harvested by centrifugation, washed in sterile PBS and concentrated to a density of 5×10$^{10}$ CFU/ml in PBS. Bacterial suspensions (5×10$^9$ CFUs in 100 µl) were gavaged into the stomach of normally colonized C57BL/6 mice every three days for three times. Arabinose 0.05% was added in the drinking water to ensure maximal expression of apyrase by pHND10 transformants. One month after the last immunization, mice were tested for anti-*Salmonella* secretory IgA as described above for *E. coli* colonized mice.

Example 1

*E. coli* in Normally Colonized Mice

Detection of Extracellular ATP Levels Produced by Commensals

Extracellular ATP had previously been detected in the supernatant of in vitro cultured intestinal commensals derived from murine faeces[5,6]. In order to address whether the metabolic activity of commensals contributed to the level of intestinal ATP, the levels of ATP in the small intestine was observed in mice from a specific pathogen free facility and in entirely germ free mice. Micromolar concentrations of ATP were detected in the specific pathogen free mice, whereas ATP was barely detectable in the entirely bacteria free mice. It was found that fluids such as urine, bile and serum which originate from sterile (or almost sterile) epithelial or endothelial organs did not demonstrate a substantial amount of endoluminal ATP (see FIG. 1(*a*)). This finding indicates that mucosal colonization by commensals plays a role in increasing extracellular ATP levels.

Figure 1C:
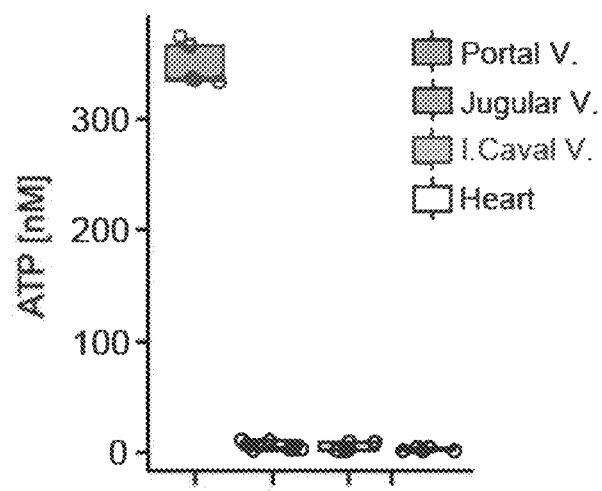
Figure 1D:
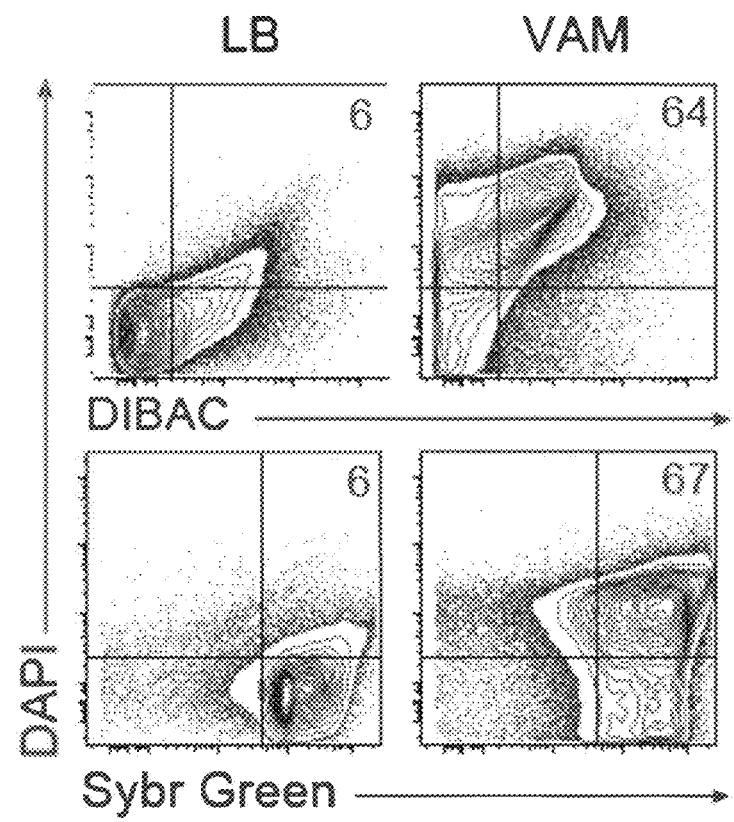
Figure 2A:
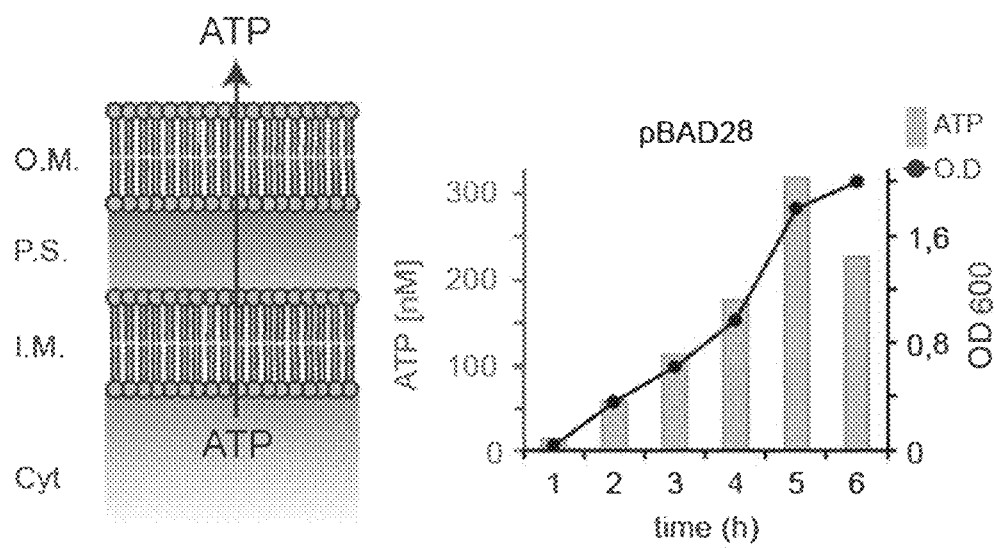
FIGS. 2A-2I Efficient induction of secretory anti-E. coli IgA response by apyrase.
Figure 2B:
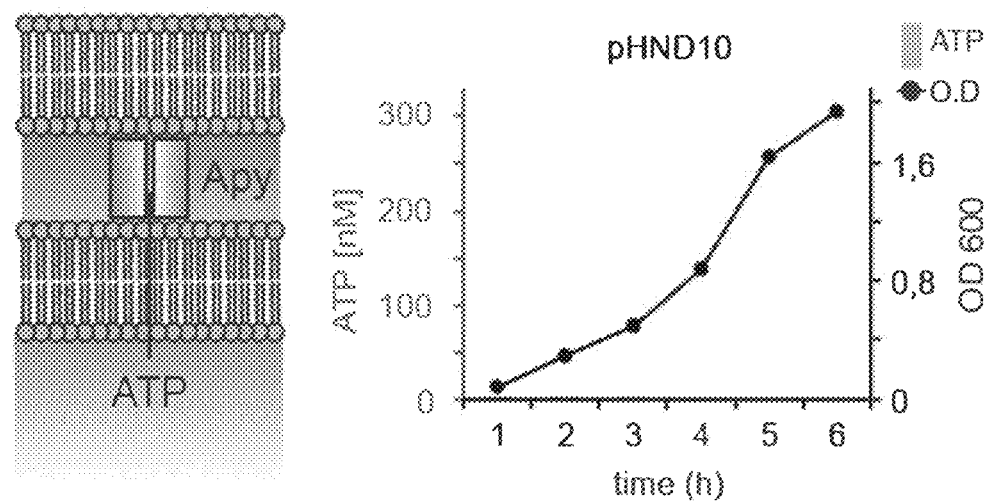
Figure 2C:
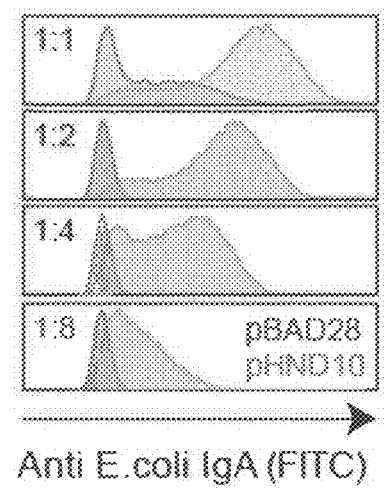
Figure 2D:
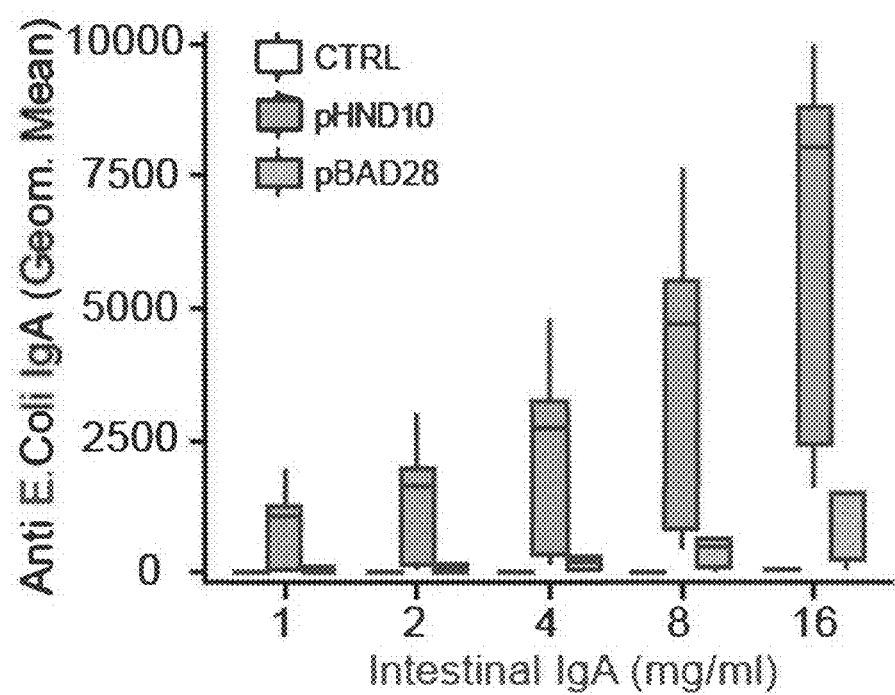
Figure 2E:
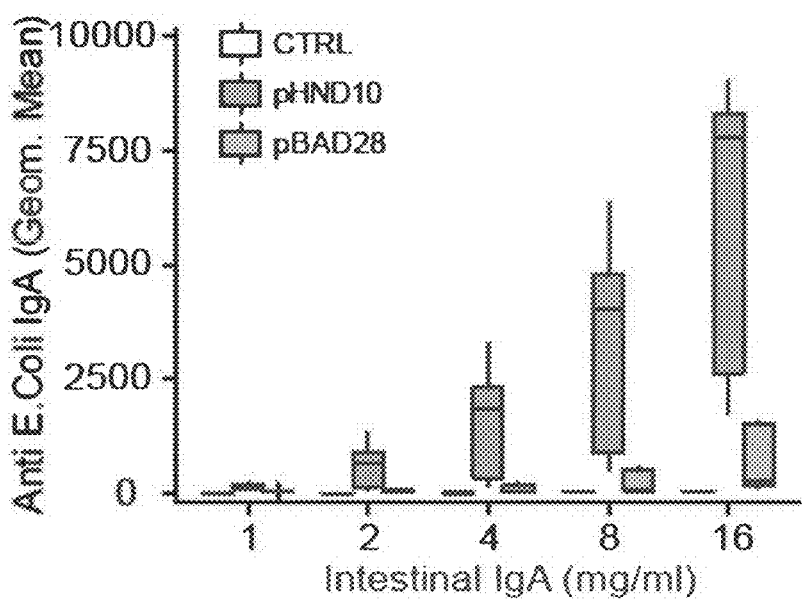
Figure 2F:
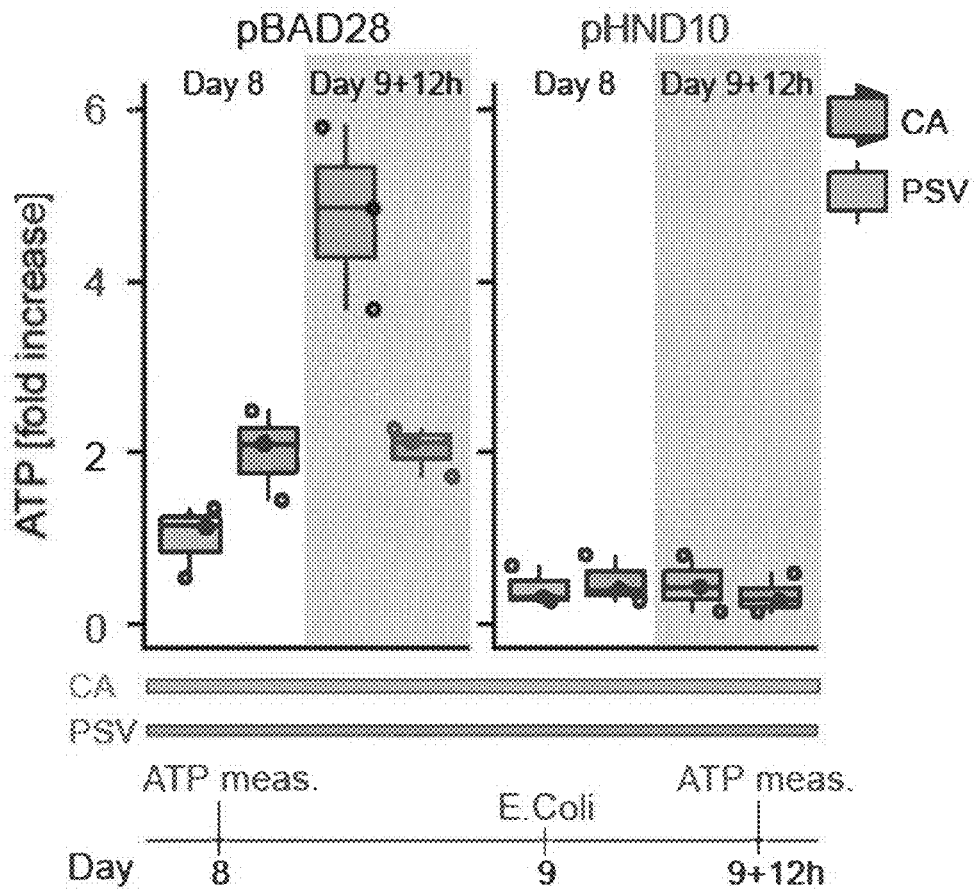
Figure 2G:
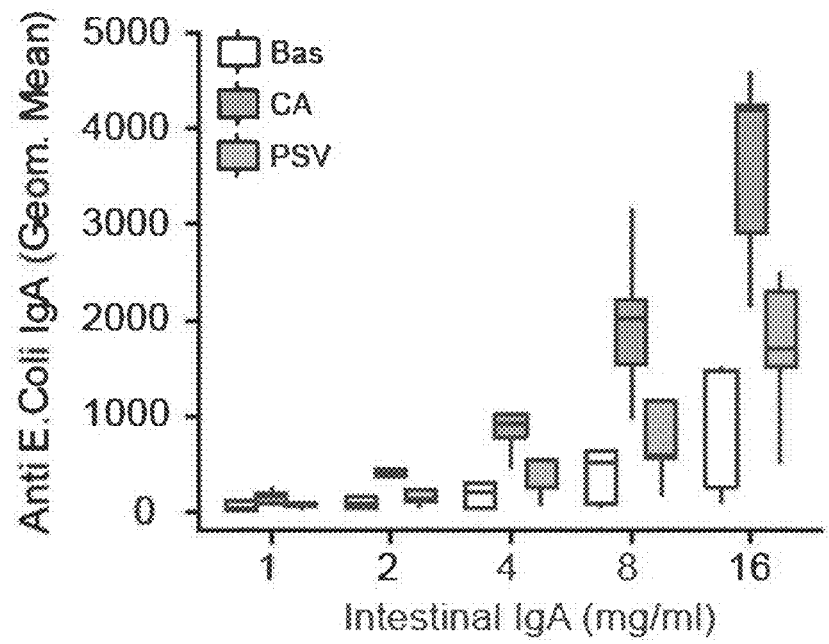
Figure 2H:
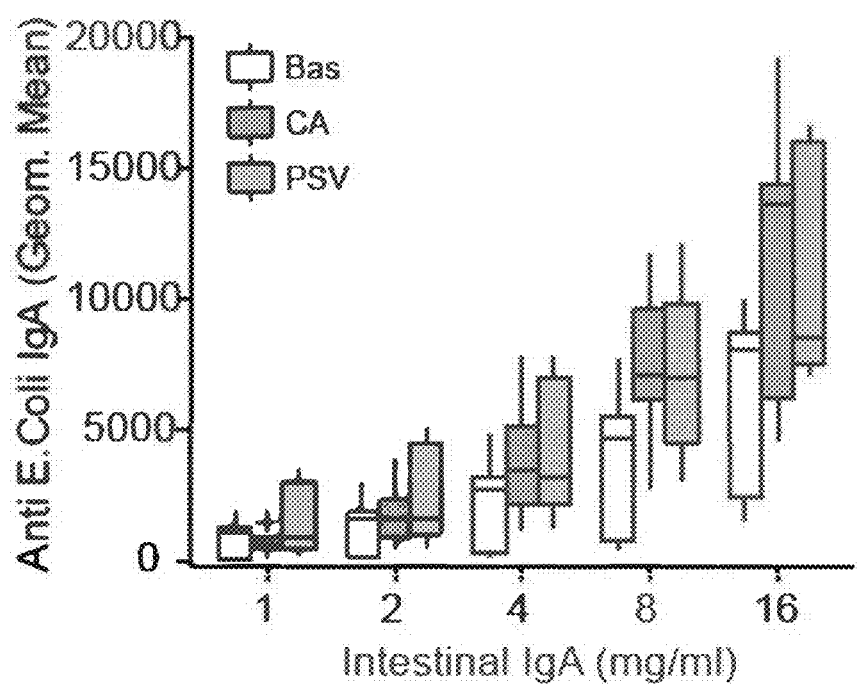
Figure 2I:
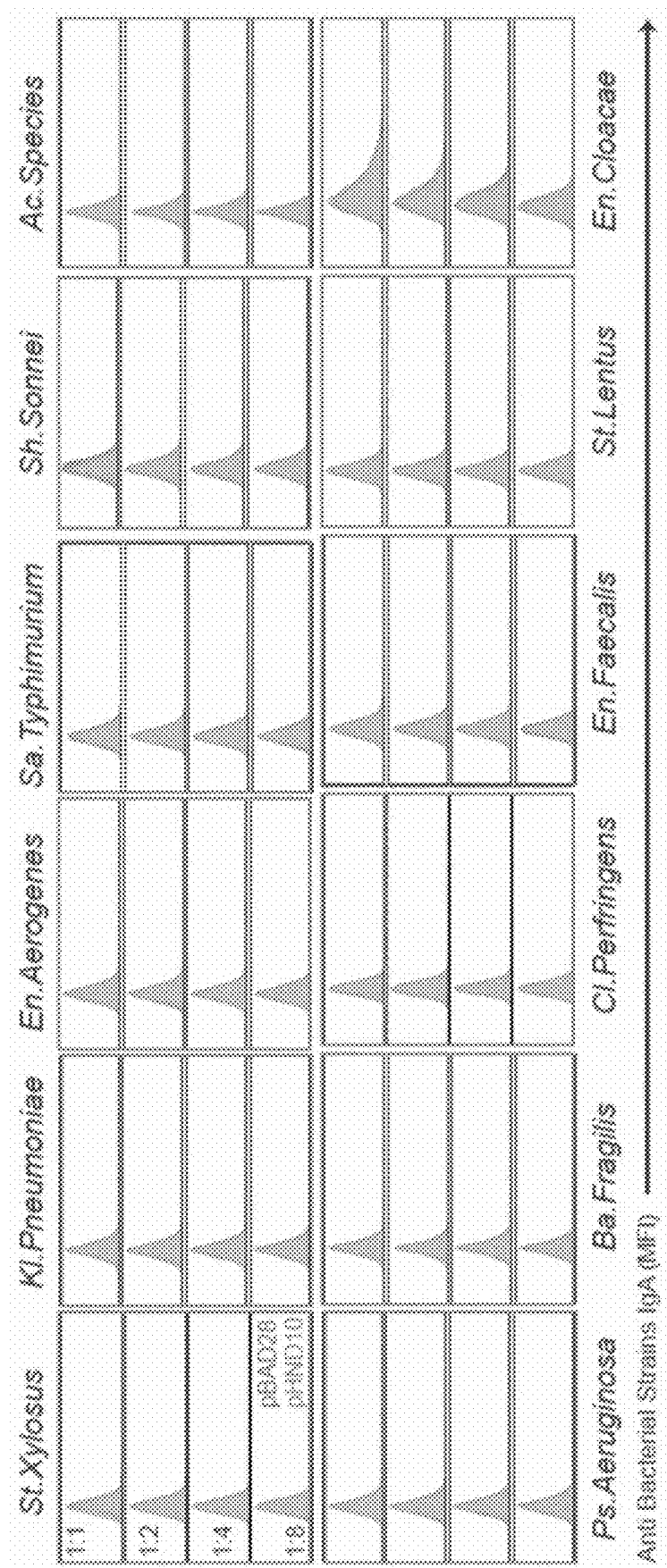
Figure 3A:
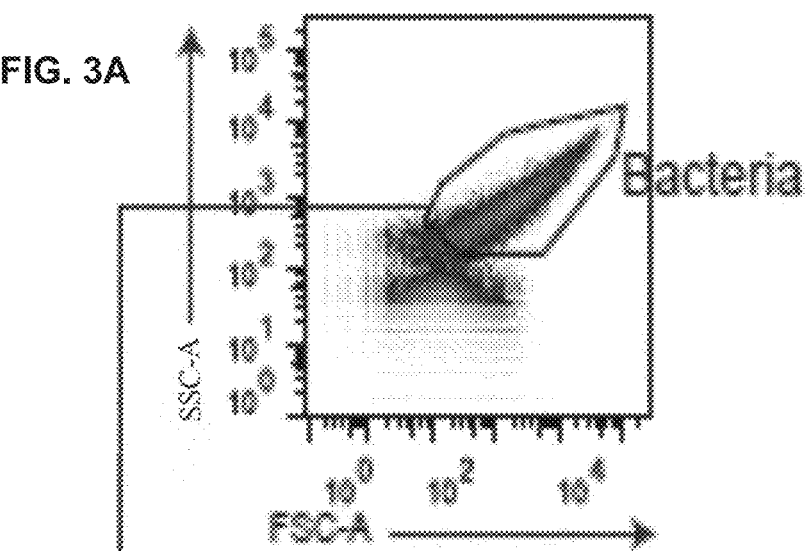
FIGS. 3A-3F Efficient induction of secretory anti-E. coli IgA response by apyrase.
Figure 3B:
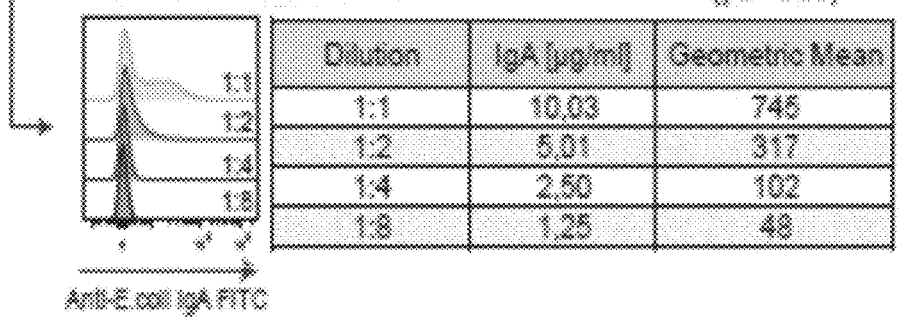
Figure 3B:
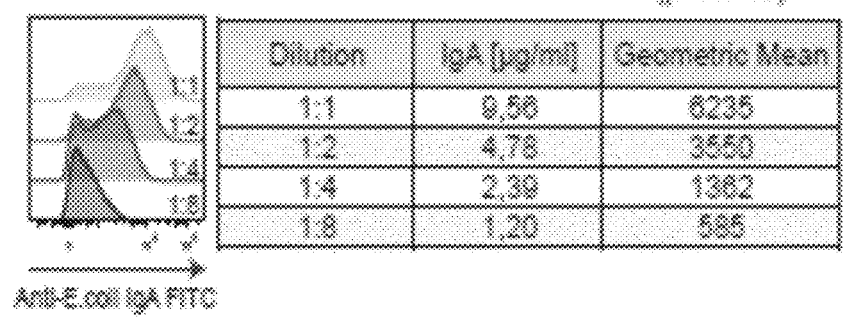
Figure 3B:
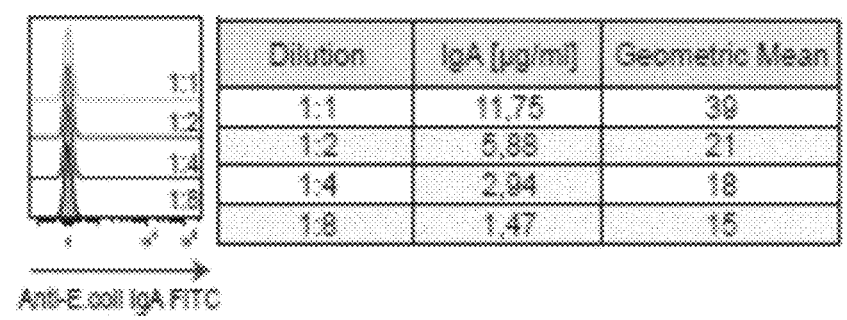
Figure 3C:
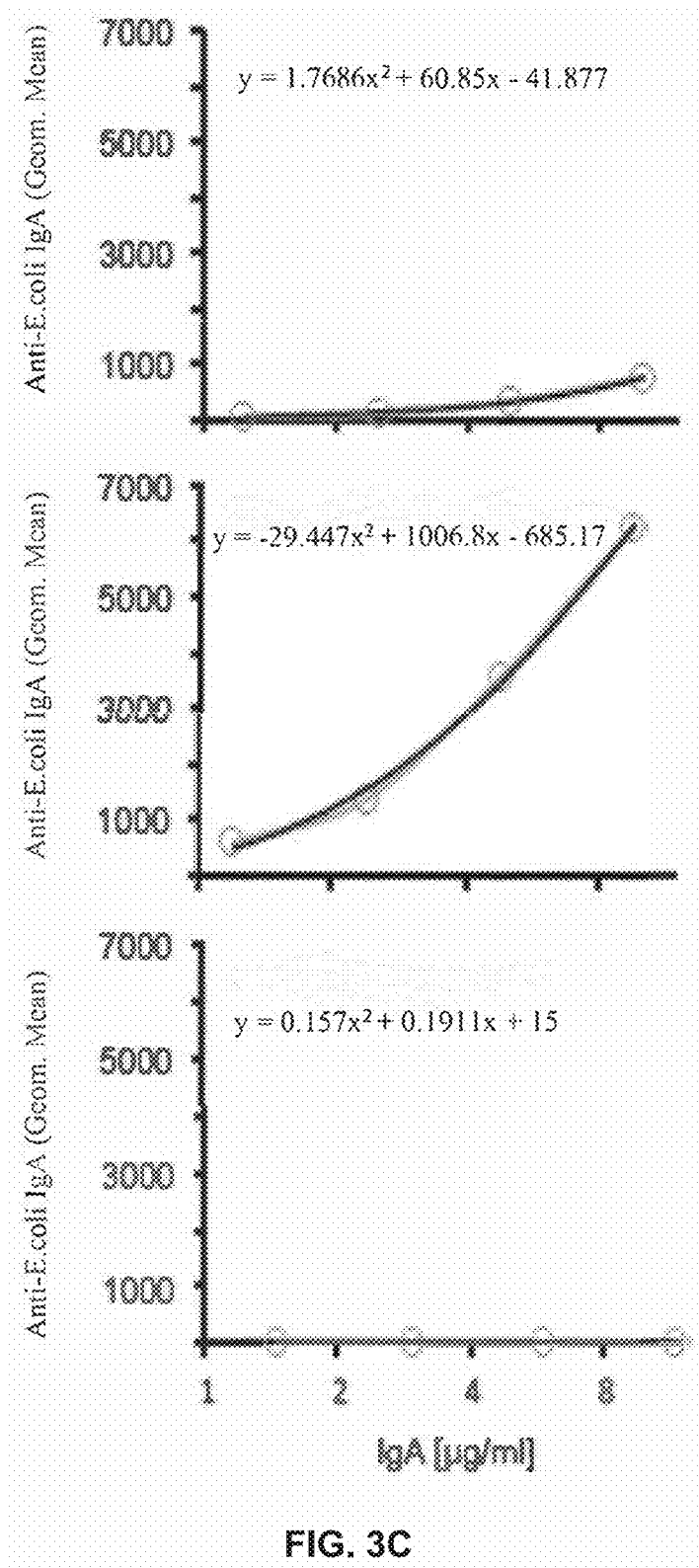
Figure 3D:
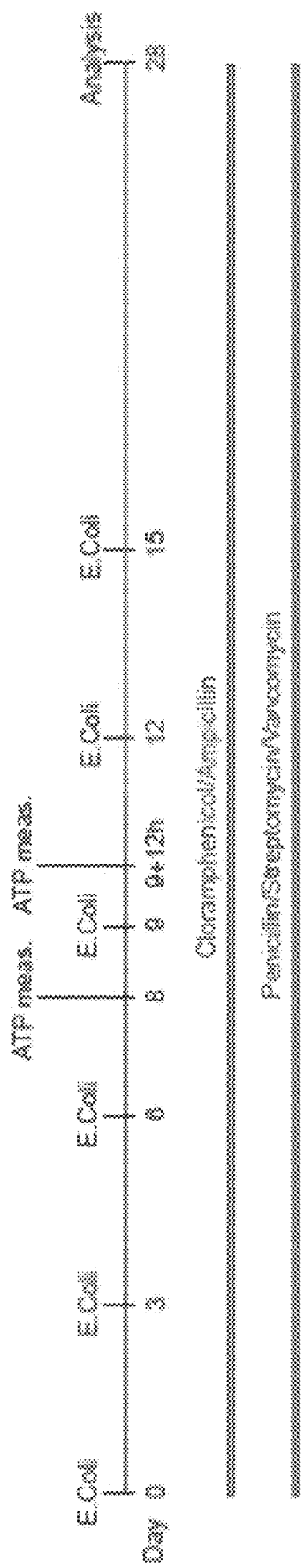
Figure 3E:
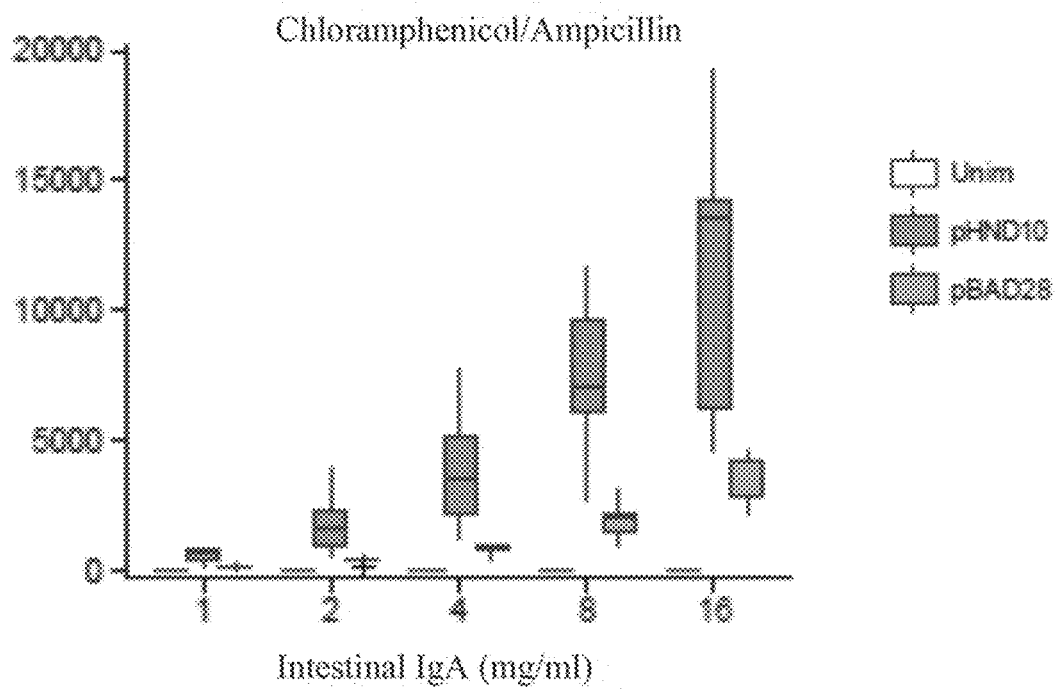
Figure 3F:
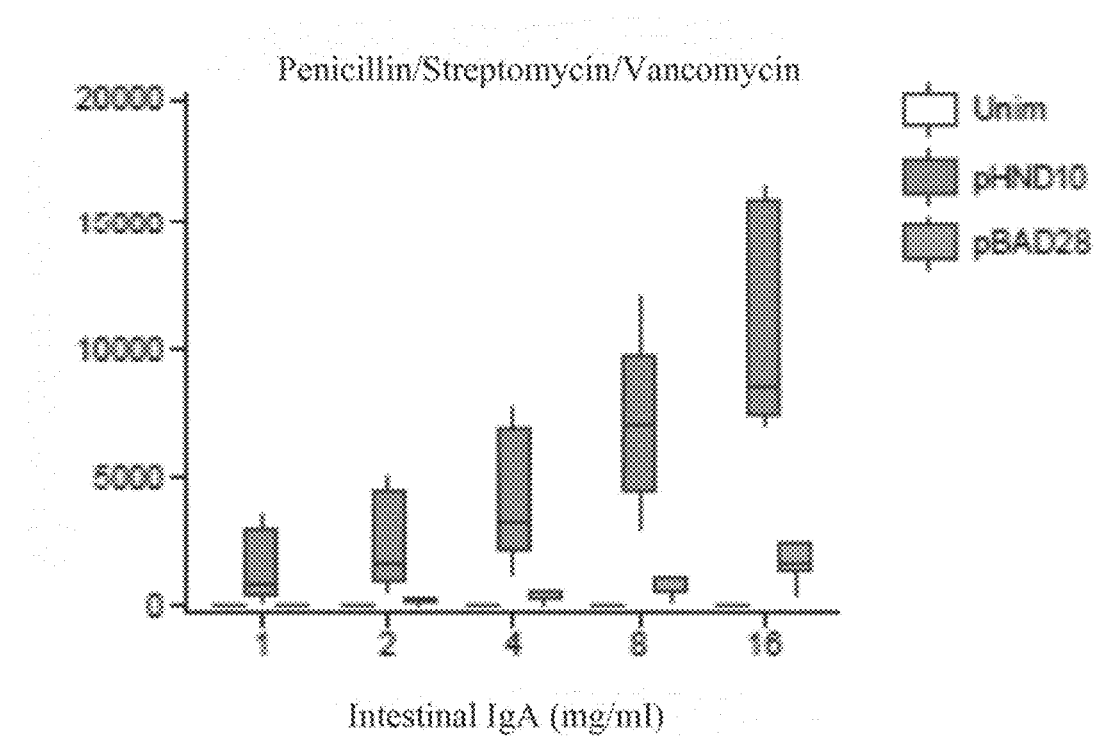

To test whether bacteria present in the small intestine release ATP, cultures of aerobic and anaerobic colonies isolated from murine ilea were tested for ATP in the medium in comparison to cell growth. FIG. 1(*b*) shows that ATP in the medium was found to increase proportionally with bacterial growth. These data therefore show that bacteria present in the small intestine contribute to the generation of luminal ATP.

The inventors also investigated whether bacterial cell death results in an additional increase in extracellular ATP due to release of ATP during cell lysis. Ileal bacterial cell cultures were treated with vancomycin, ampicillin and metronidazole (VAM). Cell death was monitored using DAPI (4',6-diamidino-2-phenylindole) staining and membrane damage was monitored using DIBAC (bis-(1,3-dibutylbarbituric acid) trimethine oxonol) staining in flow cytometry as described in reference 7. FIG. 1(*d*)-(*f*) shows that bacterial cell death and membrane permeability were associated with prominent ATP release. In vivo oral administration with VAM also resulted in an acute and significant increase in endoluminal ATP as shown in FIG. 1(*g*) in association with increased phosphatidyl serine exposure (which is a signal of cell death) in Tfh cells from Peyer's patches of wild type mice but not $P2rx7^{-/-}$ mice. This indicates that release of ATP by bactericidal death affects the abundance of Tfh cells via P2X7.

Epithelial Permeability to ATP

In order to assess epithelial permeability to ATP in the small intestine, mice were gavaged daily with ATPγS (a non-hydrolysable analogue of ATP). As Tfh cells are sensitive to extracellular ATP via P2X7 the inventors analysed Tfh cell recovery in Peyer's patches two weeks after treatment. Administration of ATPγS resulted in significant reduction of Tfh cells in wild type mice but not in $p2rx7^{-/-}$ mice. This finding suggests that luminal ATP can permeate Peyer's patches and can affect the abundance of Tfh cells via P2X7.

Analysis of ATP concentrations in blood collected from portal or jugular veins, vena cava and heart revealed a 30-50 fold increase in ATP concentration in the blood from the portal vein compared to the other samples (see FIG. 1(*c*)), indicating that ATP is readily absorbed in the small intestine.

Reducing Endoluminal ATP Levels Using Apyrase

The inventors used a recombinant *E. coli* K-12 strain expressing pHND10 (a pBAD28-based recombinant plasmid carrying the phoN2::HA fusion[8] which encodes a periplasmic apyrase (ATP-diphosphohydrolase) from *Shigella flexneri*[9].

Extracellular ATP released concomitantly with *E. coli* growth was undetectable in bacteria carrying pHND10 as shown in FIGS. 2(*a*) and (*b*), indicating that apyrase efficiently abrogated ATP secretion. Colonization of mice with pHND10 expressing *E. coli* resulted in significantly reduced ATP concentrations in the small intestine following VAM administration indicating that release of PhoN2 (apyrase) following bacterial cell death efficiently hydrolysed endoluminal ATP.

Enhancement of Antigen Specific Immune Responses

The enhancement of the anti-*E. coli* IgA response using PhoN2 was demonstrated by the inventors. C57Bl/6 mice were gavaged with *E. coli* harbouring the pHND10 plasmid and the pBAD28 plasmid (which does not encode the apyrase PhoN2). The level of *E. coli* specific IgA was significantly increased in mice gavaged with bacteria transfected with pHND10 (which encodes apyrase). Therefore ATP released by bacteria limits the development of a high affinity IgA response and reducing ATP levels by expressing apyrase as demonstrated allows a high affinity IgA response to occur as shown in FIGS. 2(*c*) and 3. Anti-*E. coli* IgA elicited by apyrase expressing bacteria was equally reactive on both pBAD28 and pHND10 containing bacteria, indicating that apyrase did not promote an "apyrase specific" IgA response (see FIGS. 2(*d*) and (*e*)).

The inventors addressed the role of apyrase as an adjuvant for high-affinity IgA response by measuring endoluminal ATP and anti-*E. coli* IgA after oral administration of chloramphenicol and ampicillin (CA; which are active on endogenous flora but not pBAD28-transformed *E. coli*) or penicillin/streptomycin/vancomycin (PSV; which are bactericidal on both endogenous and pBAD28 transformed bacteria). Anti-*E. coli* IgA in mice gavaged with pBAD28 transformed bacteria was reduced by PSV but not CA administration concomitantly with an increase in endoluminal ATP. Neither endoluminal ATP nor anti-*E. coli* IgA response were influenced by CA or PSV in mice colonized with pHND10 harboring bacteria (see FIGS. 2(*f*)-(*h*)).

The finding explained above was found to be specific to the bacterium in which the apyrase was delivered, i.e. *E. coli*. IgA antibodies specific for other bacterial species were tested for, and no increase was recorded when pHND10 harbouring *E. coli* were administered to the mice compared to when *E. coli* harbouring pBAD28 were administered as shown in FIG. 2(*i*).

Therefore, the data provided herein show that compositions comprising apyrase or another agent which is capable of reducing the level of binding of ATP to the P2X7 receptor can increase the specific IgA response to an immunogen included in the composition. Therefore, the compositions of the invention may be useful as vaccines.

Example 2

*E. coli* in Germ-Free, Monocolonized Mice

The inventors monocolonized germ-free mice in order to demonstrate the effect of apyrase on endoluminal ATP levels, Tfh and germinal centre cell number and anti-*E. coli* IgA levels in a controlled experimental setting, in which the same amount of bacterial stimuli were present in the gut apart from extracellular ATP.

Reducing Endoluminal ATP in the Presence of Apyrase in Monocolonized Mice

Figure 4:
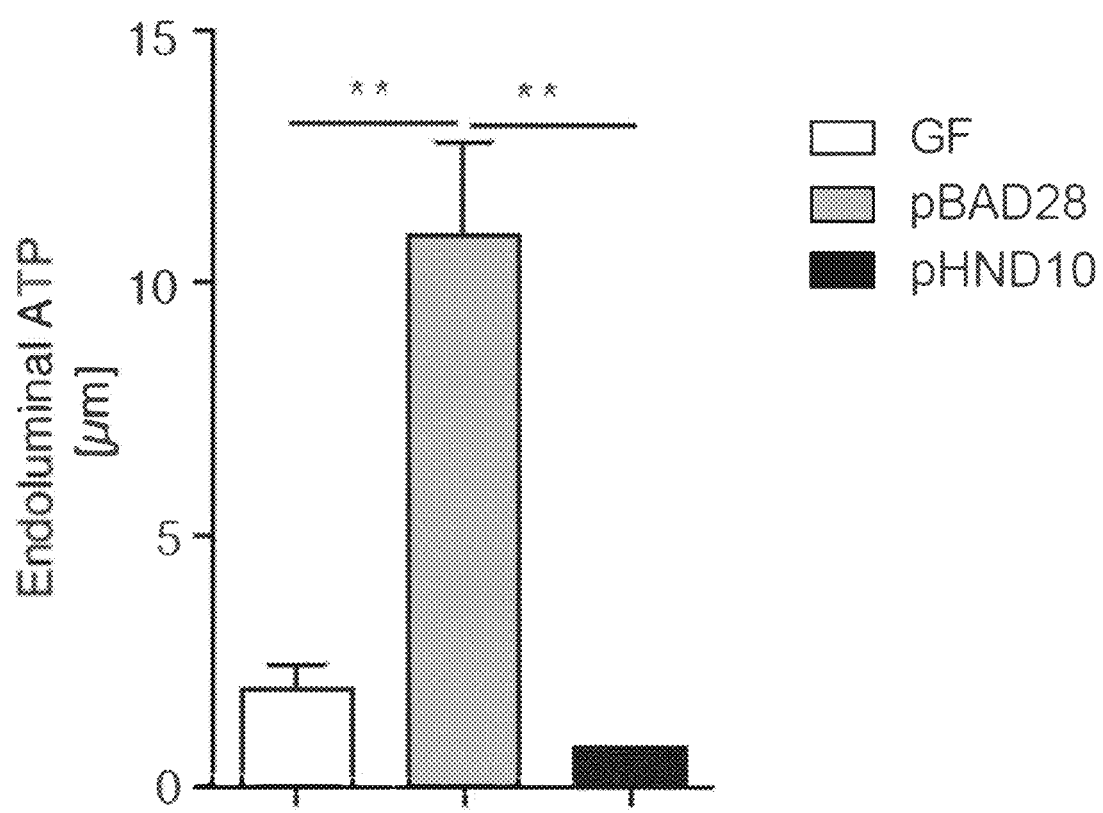
FIG. 4 Endoluminal ATP levels in germ-free mice monocolonized with pBAD28 harbouring E. coli (middle bar), pHND10 harbouring E. coli (right bar), and control germ-free mice (GF; left bar).

Germ-free mice were monoclolonized by E. coli transformed with pHND10 or pBAD28. FIG. 4 shows that mice monocolonized with pHND10 harbouring E. coli showed significantly reduced concentration of endoluminal ATP in the intestine compared to mice monocolonized with pBAD28 harbouring E. coli and control mice. Germ-free mice which were not colonized with E. coli were used as a control.

Figure 5:
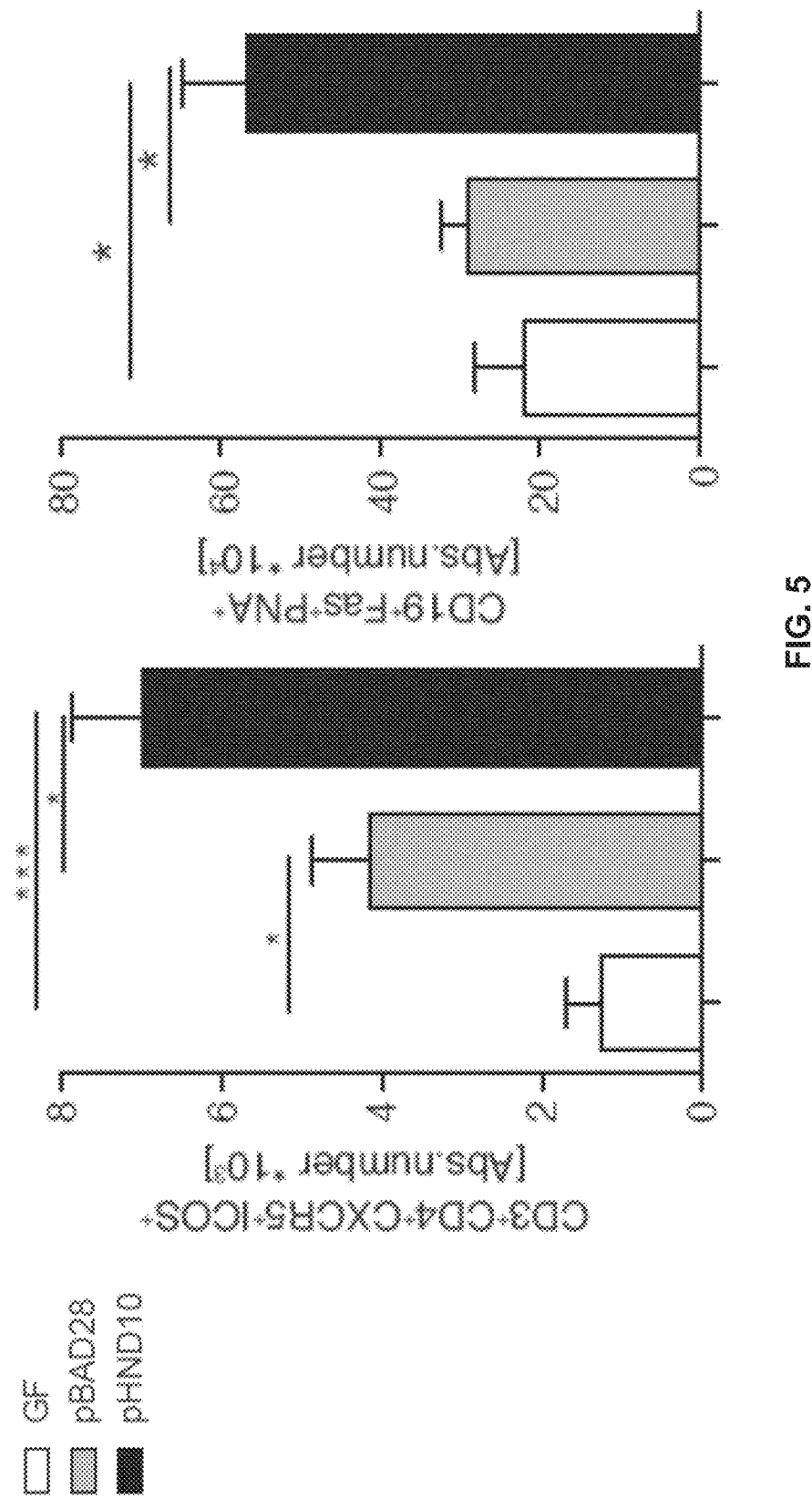
FIG. 5 Analysis of Tfh cell number (left graph) and germinal centre cell number (right graph) in animals monocolonized with pBAD28 harbouring E. coli (middle bars), pHND10 harbouring E. coli (right bars) and control germ-free mice (GF; left bars).

Number of Tfh Cells and Germinal Centre B Cells are Increased in the Presence of Apyrase in Monocolonized Mice Germ-free mice monocolonized with E. coli transformed with either pHND10 or pBAD28 were tested for number of Tfh cells ($CD3^+CD4^+CXCR5^+ICOS^+$) and number of germinal centre B cells ($CD19^+Fas^+PNA^+$) by enumerating total cells in the Peyer's patches and extrapolating relative abundances of Tfh and GC B cells by their frequencies at FACS. FIG. 5 shows that the number of Tfh cells and germinal centre B cells were increased in mice monocolonized with pHND10 harbouring E. coli compared with mice monocolonized with pBAD28 harbouring E. coli or control mice.

This finding is consistent with endoluminal ATP having a role in regulating Tfh cell and germinal centre B cells in the Peyer's patches of the small intestine. The presence of apyrase expressed in the pHND10 harbouring E. coli reduces levels of endoluminal ATP, which prevents ATP from reducing the number of Tfh cells and germinal centre cells.

Anti-E. coli IgA is Increased in the Presence of Apyrase in Monocolonized Mice

Figure 6:
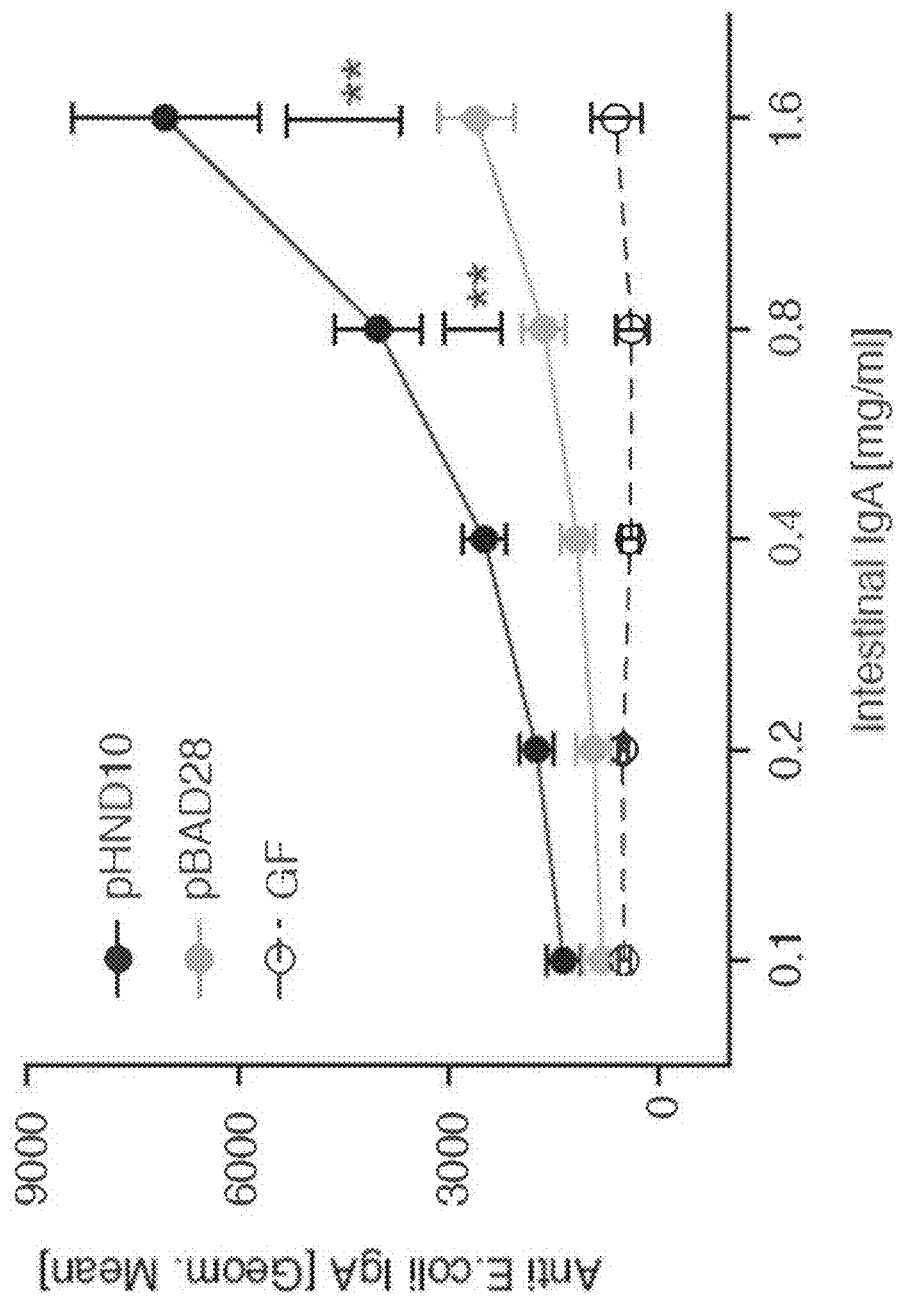
FIG. 6 Geometric mean of anti-E. coli IgA in intestinal fluid by FACS plotted against total intestinal IgA concentration, from germ-free mice monocolonized with pBAD28 harbouring E. coli, germ-free mice colonized with pHND10 harbouring E. coli and control germ-free mice (GF).

Germ-free mice monocolonized with E. coli transformed with either pHND10 or pBAD28 were tested for anti-E. coli IgA as described above. FIG. 6 shows that the level of E. coli specific IgA was significantly increased in mice monocolonized with pHND10 compared with mice monocolonized with pBAD28 or control mice.

This finding confirms that the IgA produced as a result of the presence of apyrase is specific to an immunogen administered simultaneously with the apyrase.

Example 3

Attenuated *Salmonella typhimurium* in Normally Colonized Mice

Generating *Salmonella typhimurium* which Expresses Apyrase

Figures 7A, 7B:
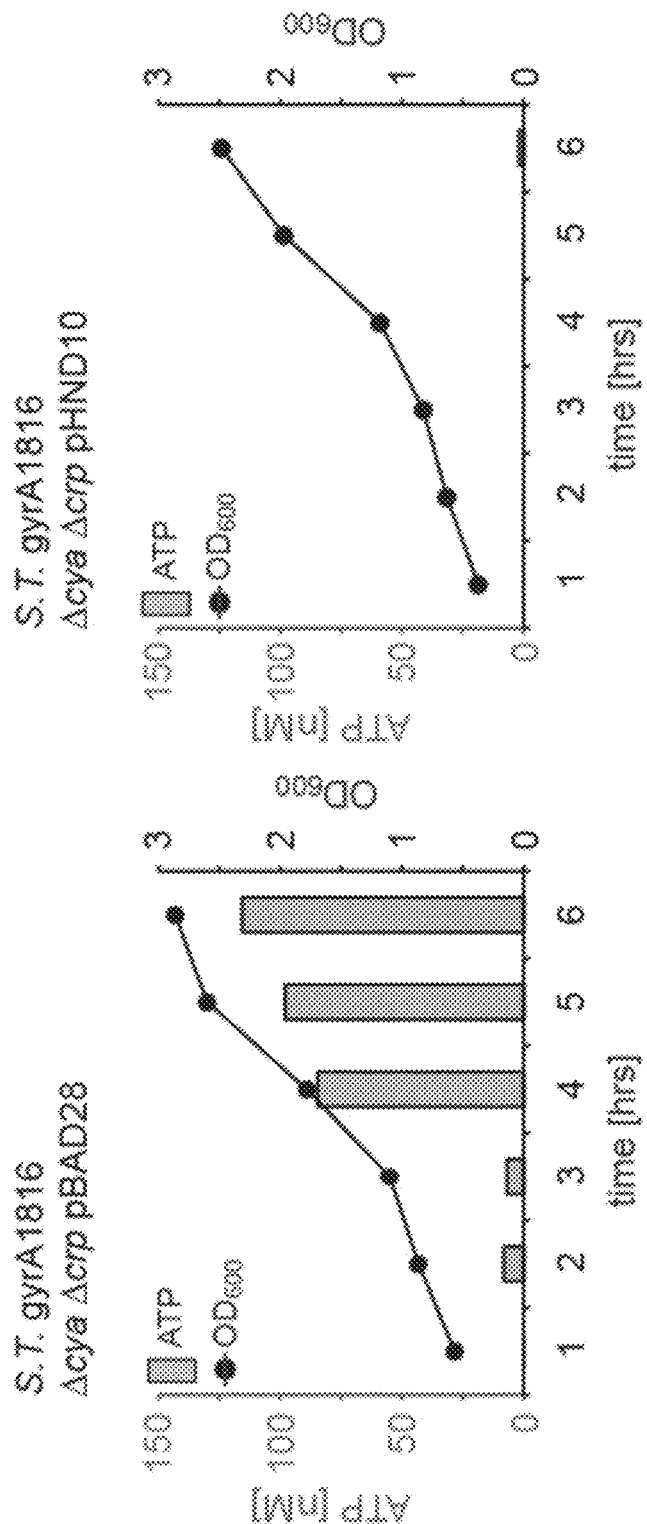
FIGS. 7A-7B ATP concentrations (bars) in culture medium and bacterial growth ($OD_{600}$) over time for pBAD28 harbouring (FIG. 7A) or pHND10 harbouring (FIG. 7B) avirulent S. typhimurium.

To address whether apyrase expression in live attenuated *Salmonella typhimurium* could increase the specific IgA response and confer enhanced protection from infection by a virulent strain, the inventors used avirulent gyrA1816 Δcya1 Δcrp1 *Salmonella typhimurium* (ATCC® 53648™) (which includes mutations in cya and crp genes and is incapable of producing functional adenylate cyclase as well as cyclic AMP receptor protein) as a model vaccine. The inventors transformed *S. typhimurium*, with either pBAD28 or pHND10, as described above. As observed in E. coli, FIG. 7 shows that ATP was undetectable in culture medium of *S. typhimurium* carrying pHND10 (and therefore expressing apyrase) (see FIG. 7b) but was detected in increasing amounts that correlated with bacterial cell density in *S. typhimurium* carrying pBAD28 (and therefore not expressing apyrase) (see FIG. 7a).

Anti-*S. typhimurium* IgA is Increased in the Presence of Apyrase

Figure 8:
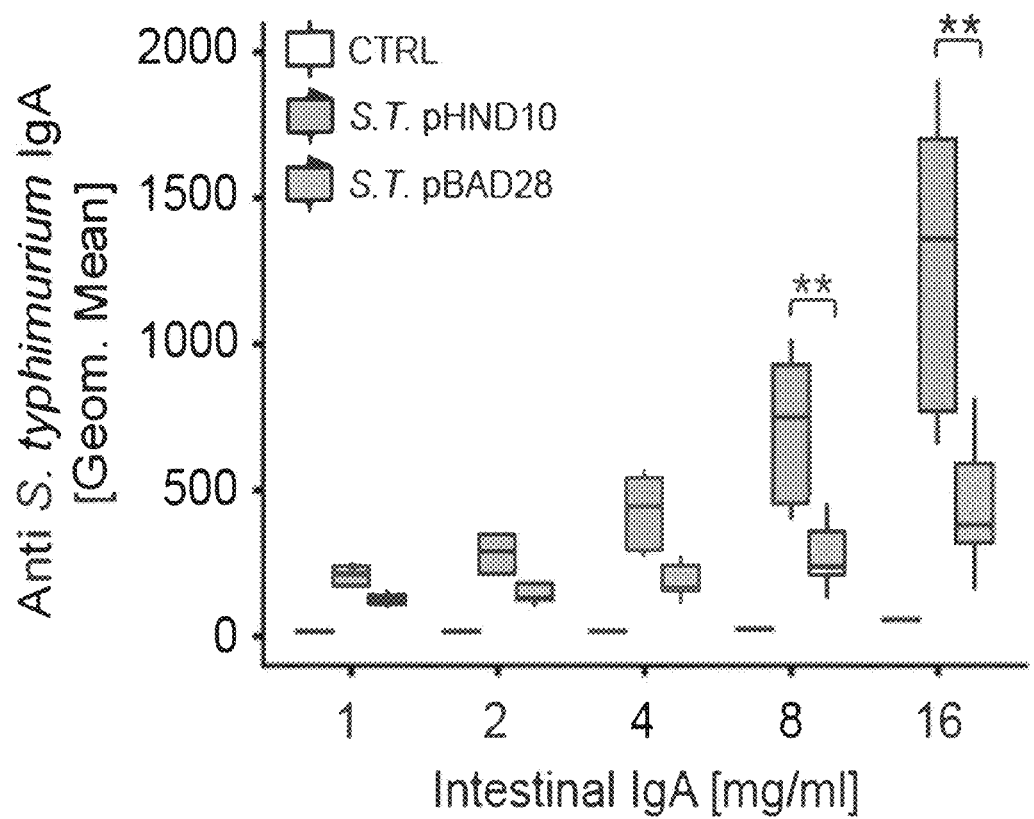
FIG. 8 Geometric mean of anti-S. typhimurium IgA in intestinal fluid by FACS plotted against total intestinal IgA concentration, from control mice (left bars), mice immunized with pHND10 harbouring attenuated S. typhimurium (middle bars) and mice immunized with pBAD28 harbouring attenuated S. typhimurium (right bars).

Normally colonized mice were immunized by gavage every three days for three times with $5\times10^9$ avirulent *S. typhimurium* transformed with either pHND10 or pBAD28. Arabinose 0.05% was added to the animals' drinking water to ensure maximal expression of apyrase by pHND10 transformants during immunization. After one month from the last immunization mice were tested for anti-*Salmonella* secretory IgA as described above for E. coli colonized mice. FIG. 8 shows that the *Salmonella* specific IgA response was significantly increased in mice immunized per os with pHND10 carrying attenuated *S. typhimurium* as compared to attenuated *S. typhimurium* carrying pBAD28 or control mice.

This finding confirms that the IgA produced as a result of the presence of apyrase is specific to the immunogen administered simultaneously with the apyrase.

Immunization with Attenuated *S. typhimurium* Carrying Apyrase Protects against Virulent *S. typhimurium*

Figure 9:
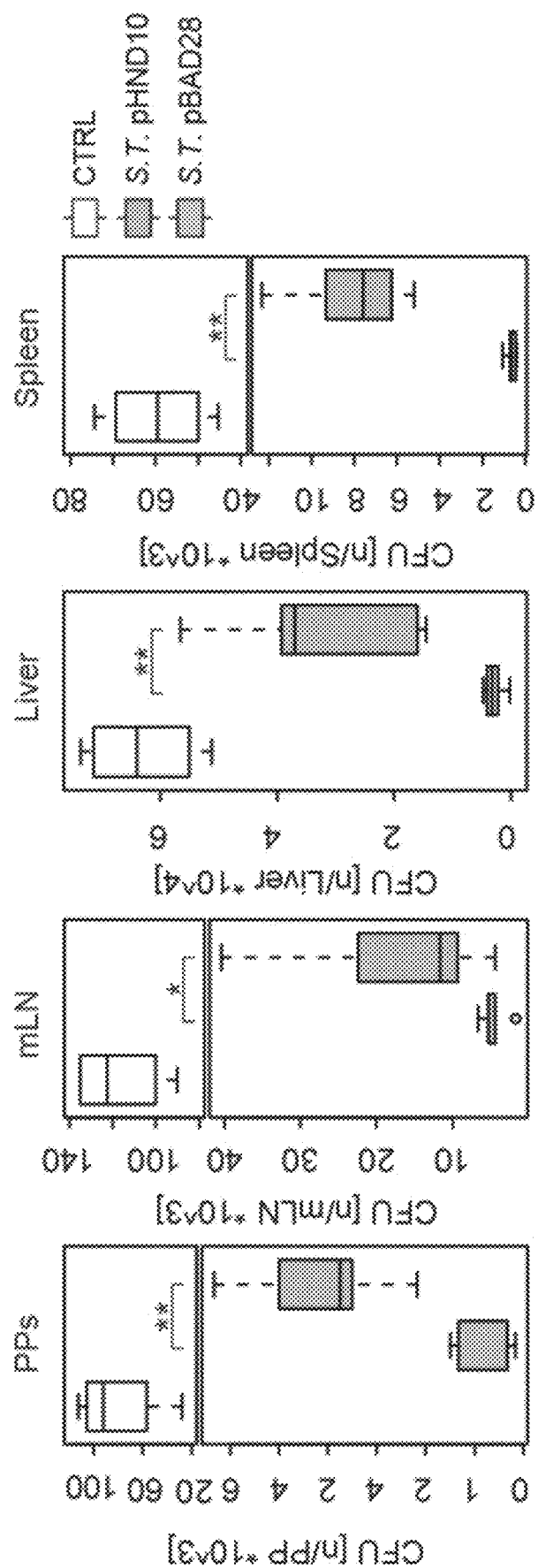
FIG. 9 Recovery of virulent Salmonella from PPs, mesenteric lymph nodes (MLNs), spleen and liver in control non immunized mice (left bars), mice immunized with pHND10 harbouring attenuated S. typhimurium (middle bars) and mice immunized with pBAD28 harbouring attenuated S. typhimurium (right bars). CFU, colony forming unit; CTRL, non-immunized mice.

Colonization resistance by commensal flora limits infection with virulent *S. typhimurium*. In contrast, pretreatment of mice with streptomycin allows efficient development of enterocolitis and typhoid. Immunization of mice with attenuated *S. typhimurium* transformed with either pHND10 or pBAD28 was tested for its ability to protect against infection by $5\times10^7$ virulent *Salmonella* (*s. Tm$^{wt}$*: SB300 *S. enterica* serovar Thyphimurium SL1344 (wildtype) resistant to streptomycin, as disclosed in reference 10) upon streptomycin administration at one month from the last immunization. Infection of mice that have been previously immunized with avirulent *Salmonella* bearing pHND10 resulted in significantly reduced recovery of virulent *Salmonella* from Peyer's patches and barely detectable levels of virulent *Salmonella* in mesenteric lymph nodes (MLNs), spleen and liver when compared with mice immunized with pBAD28 transformants or control non-immunized mice at 48 h post-infection (see FIG. 9).

Figure 10A:
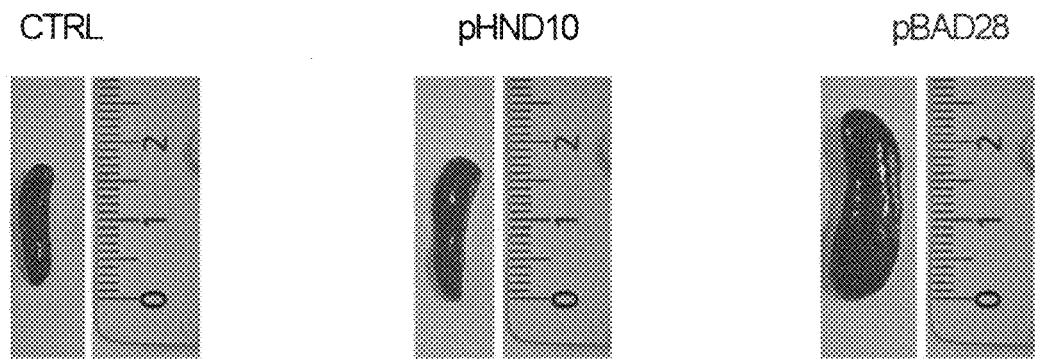
FIGS. 10A-10B (FIG. 10A) Spleen size in mice immunized with attenuated Salmonella bearing pBAD28 or pHND10 and then challenged with virulent Salmonella, compared with control untreated mice.
Figure 10B:
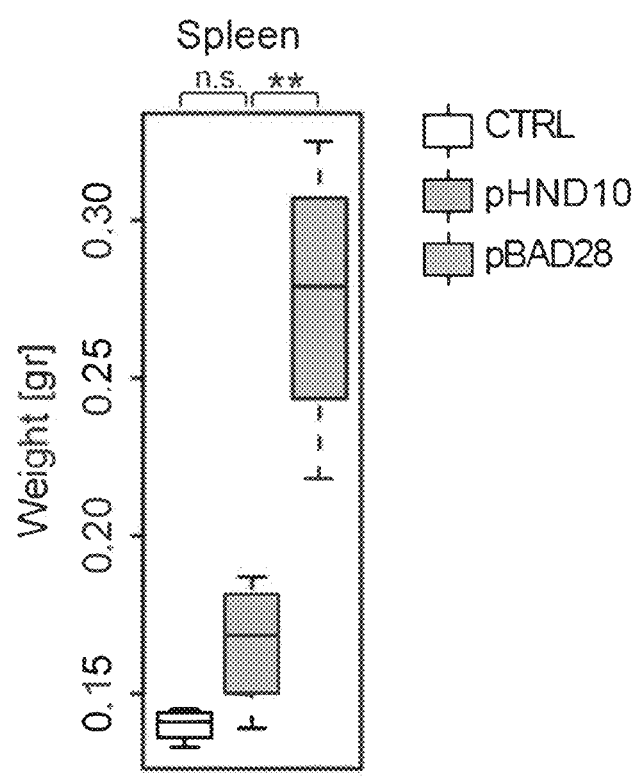
Figure 11A:
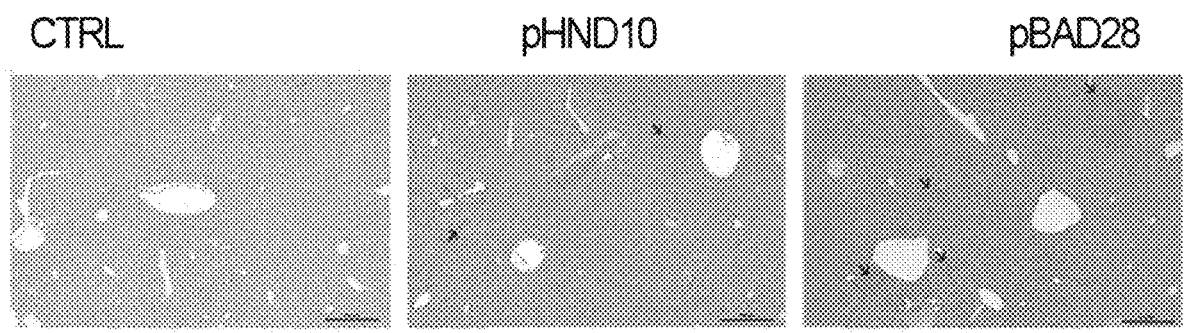
FIG. 11A-11B.
Figure 11B:
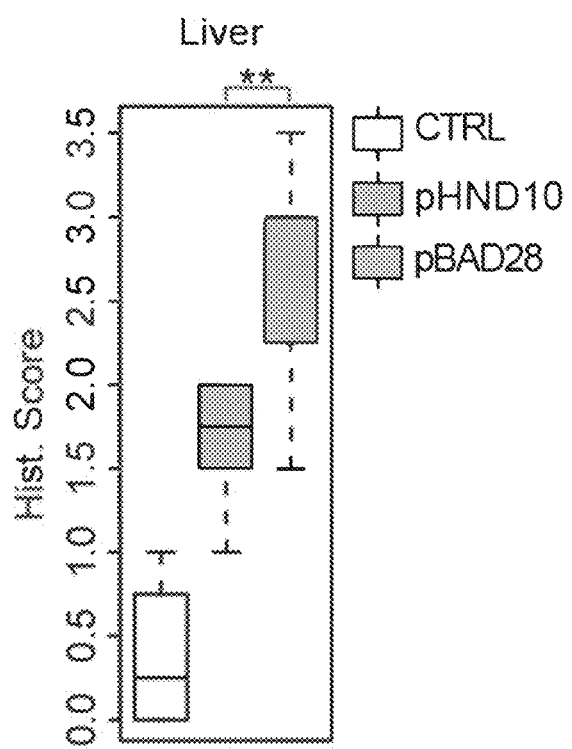

This is consistent with the decrease in pathophysiological changes following infection observed in mice immunized with pHND10 containing attenuated *S. typhimurium* compared with mice immunized with pBAD28 containing *S. typhimurium* or non-immunized mice. FIG. 10 shows that spleen size and weight is greatly increased in infected mice immunized with pBAD28 harbouring *S. typhimurium* but not in infected mice immunized with pHND10 harbouring attenuated *S. typhimurium* as compared to a control spleen of untreated mice. FIG. 11 shows that liver histology is worsened in infected mice immunized with pBAD28 harbouring *S. typhimurium* but not in infected mice immunized with pHND10 harbouring attenuated *S. typhimurium* as compared to a control liver of untreated mice.

A further way in which the inventors demonstrated that immunization with pHND10 containing attenuated *S. typhimurium* resulted in protection from virulent *Salmonella* was by monitoring the extent to which infection with virulent *Salmonella* causes leaking of the gut endothelial barrier. This leakage was monitored by analyzing the permeability of the gut to dextran administered to the mice by gavage. To this end, C57BL/6J mice immunized with avirulent *Salmonella* were orally infected with $5\times10^7$ virulent *Salmonella* and gavaged with 5 mg of 70 KDa FITC-dextran. After 4 hours peripheral blood was collected and tested for the presence of the fluorophore in the serum. From each value, background fluorescence value of serum collected from untreated mice was subtracted.

Mice that have been effectively protected from the effects of virulent *Salmonella* infection do not display gut permeability to dextran therefore sera from such mice contain less dextran that mice suffering from the effects of virulent *Salmonella* infection (i.e. which have been less efficiently protected).

Figure 12:
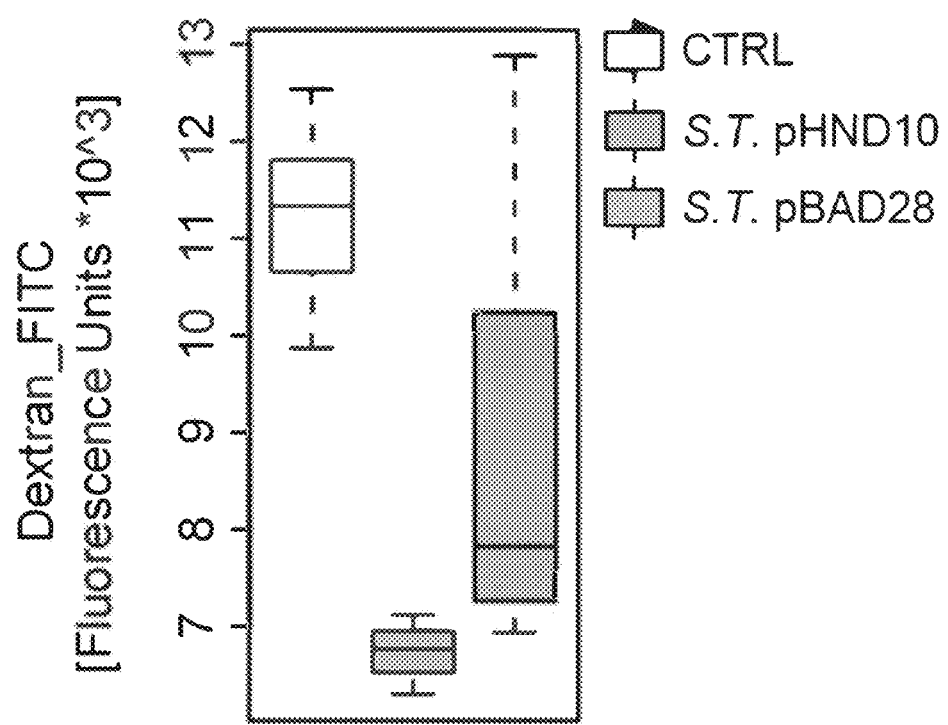
FIG. 12 Dextran amounts in mice immunized with pHND10 harbouring attenuated S. typhimurium (middle bar), non-immunized mice (CTRL; left bar) and mice immunized with pBAD28 harbouring attenuated S. typhimurium (right bar), after infection with virulent S. typhimurium.

FIG. 12 shows that sera from mice immunized with pHND10 harbouring attenuated *S. typhimurium* contained significantly reduced amounts of dextran after infection with virulent *S. typhimurium* compared with control non-immunized mice and mice immunized with pBAD28 harbouring attenuated *S. typhimurium*. These results indicate that the IgA response provided by immunization with apyrase-expressing bacteria confers protection from systemic spreading of *Salmonella*.

Figure 13:
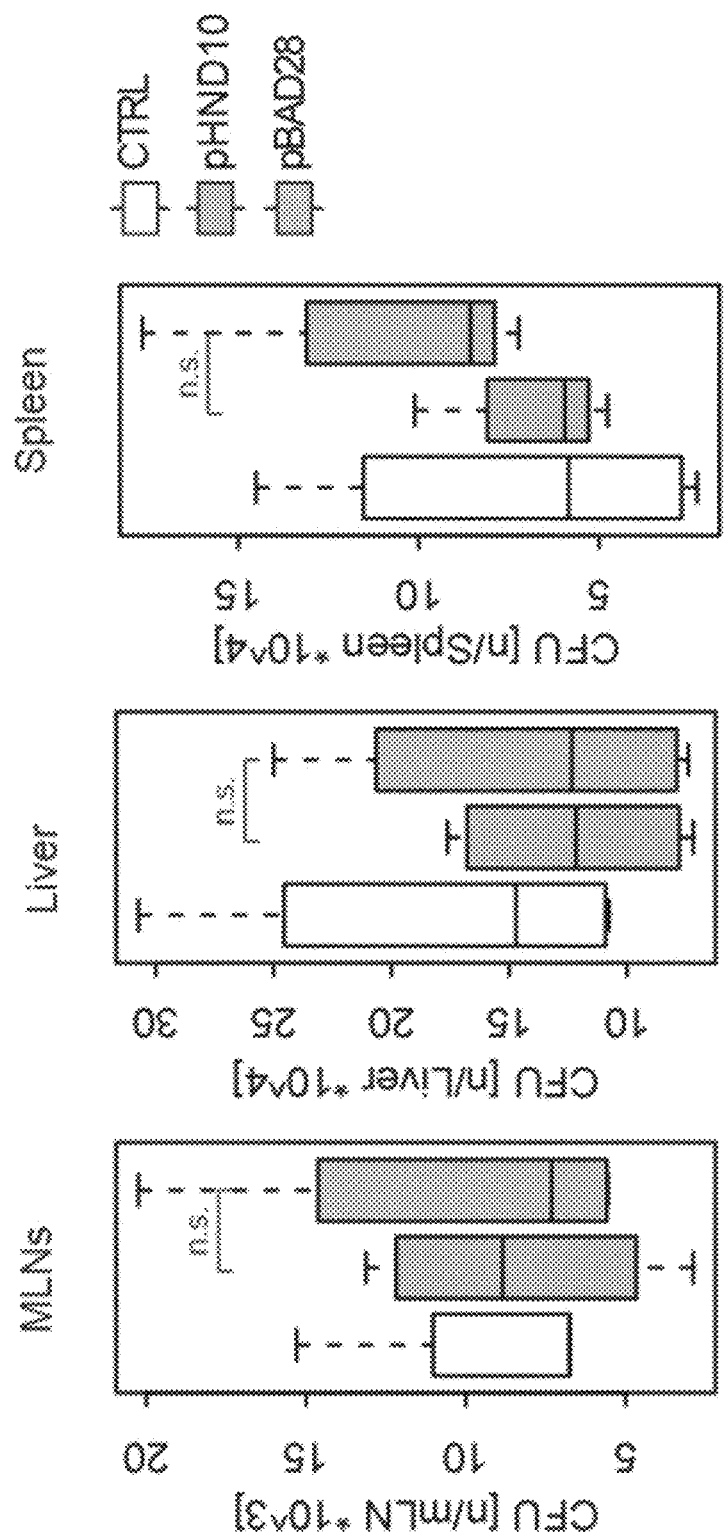
FIG. 13 Numbers of virulent *Salmonella* colony forming units (CFUs) recovered in mesenteric lymph nodes (MLNs), liver and spleen from recombinase-activating gene-1 (Rag-1) deficient mice at 48 hours after challenge with virulent *Salmonella*. Non-immunized mice (CTRL) are represented by the left bars, mice immunized with pBAD28 harbouring attenuated *S. typhimurium* by the right bars and mice immunized with pHND10 harbouring attenuated *S. typhimurium* by middle bars.

Adaptive IgAs are Responsible for the Protection Observed in the Presence of Apyrase The inventors immunized recombinase-activating gene-1 (Rag-1) deficient mice with attenuated *S. typhimurium* carrying either pBAD28 or pHND10, as described above for C57BL/6 mice, in order to observe the effect that such immunization had on mice unable to produce mature B or T lymphocytes. The presence of apyrase (in mice immunized with attenuated *S. typhimurium* carrying pHND10) did not result in enhanced protection from infection with virulent *Salmonella* as shown in FIG. 13 by comparable numbers of virulent *Salmonella* colony forming units (CFUs) recovered in mesenteric lymph nodes (MLNs), liver and spleen from control non-immunized mice or mice immunized with pBAD28 or pHND10 harbouring *S. typhimurium* at 48 h after challenge with virulent *Salmonella*. These results indicate that lymphocytes (e.g. adaptive IgAs) are responsible for the observed protection by immunization in wild-type mice.

It will be understood that the invention has been described by way of example only and modifications may be made whilst remaining within the scope and spirit of the invention.

Example 4

Treatment of Mice with an Apyrase Composition in the Absence of an Immunogen in the Form of a Bacterial Carrier Extraction of Periplasmic Proteins

*E. coli* transformed with pBAD28 or pHND10 were aseptically inoculated into LB medium containing arabinose (0.3%) and ampicillin (100 μg/ml), and incubated at 37° C. for 18 hours. Bacteria ($10^{11}$) were spun at 6000 rpm for 20 min at 4° C., washed twice in PBS, resuspended in 1 ml of 30 mM Tris-HCl (pH 8.0), 4 mM EDTA, 1 mM PMSF, 20% sucrose and 0.5 mg/ml lysozyme and incubated for 3 min at 30° C.; then, $MgCl_2$ was added at a final concentration of 10 mM and bacteria incubated for 1 h a 30° C. Bacteria suspension was centrifuged at 10'000 rpm for 10 min at 4° C. and 100 μl supernatant (i.e. periplasmic proteins) administered to C57BL/6 mice by gavage.

Fecal IgA Increased in Mice Treated with Periplasmic Proteins from Apyrase Bearing *E. coli*

Fecal IgA concentrations were measured in mice that were either untreated or gavaged daily for 15 days with periplasmic proteins from arabinose induced pBAD28 (empty vector) or pHND10 (apyrase bearing vector) *E. coli* transformants.

Figure 14:
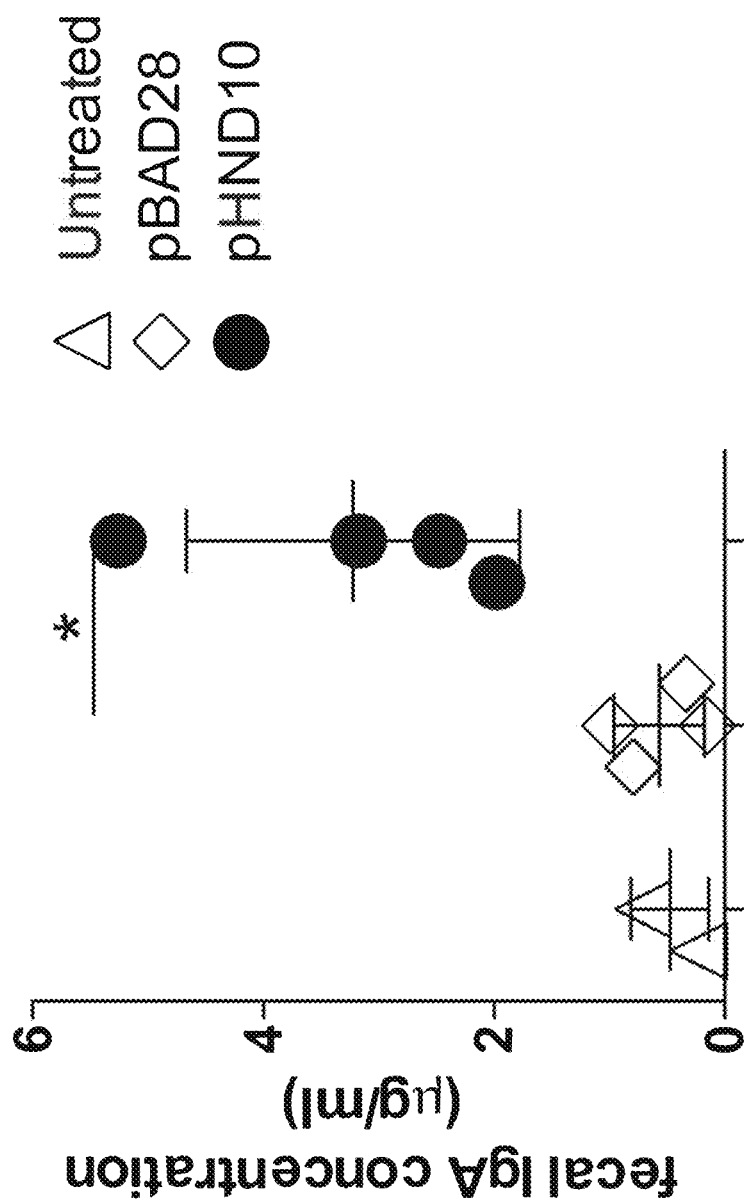
FIG. 14 Fecal IgA concentrations in untreated mice (left bar—represented by triangles), mice treated with periplasmic proteins from pBAD28 bearing *E. coli* (middle bar—represented by diamonds) and mice treated with periplasmic proteins from pHND10 bearing *E. coli*.

FIG. 14 shows that mice treated with an apyrase containing composition have increased fecal IgA compared with untreated mice or mice treated with a non-apyrase containing composition. These data indicate that apyrase is capable of providing an IgA immune response within an immunologically inert composition in the gut (as shown by lack of modification of IgA concentration by periplasmic proteins from pBAD28 transformants) and in the absence of an immunogen in the form of a bacterial carrier.

REFERENCES

[1] Proietti et al. (2014) *Immunity* 41, 789-801
[2] Kay et al. (2003) *Nature*. 424: 251
[3] Gennaro (2000) *Remington: The Science and Practice of Pharmacy*. 20th edition, ISBN: 0683306472.
[4] Hapfelmeier et al., (2010)
[5] Atarashi, K. et al. (2008) *Nature* 455, 808-812
[6] Iwase, T. et al. (2010) *J Clin Microbiol* 48, 1949-1951
[7] Maurice, C. F. & Turnbaugh, P. J. (2013) *Methods in enzymology* 531, 91-107
[8] Scribano, D. et al. (2014) *PloS one* 9, e90230
[9] Santapaola, D. et al. (2006) *Journal of bacteriology* 188, 1620-1627
[10] Hoiseth, S. K. and Stocker, B. A. (1981) *Nature* 291: 238-239

The invention claimed is:

1. A method of enhancing and/or eliciting an immune response in a subject, the method comprising administering a composition capable of enhancing an IgA immune response and/or an IgG immune response comprising an ATP-hydrolysing enzyme and an immunogen to the subject, wherein the composition is administered to the subject orally, and wherein the immunogen is a bacterial antigen, a parasitic antigen or a viral antigen capable of eliciting an immune response against a gastrointestinal pathogen or a mucosally transmitted systemic pathogen.

2. The method of claim 1, where the ATP-hydrolysing enzyme is apyrase.

3. The method of claim 2, wherein the apyrase is *Shigella flexneri* apyrase.

4. The method of claim 1, wherein the immunogen is capable of eliciting an immune response against a pathogen selected from the group consisting of *Vibrio cholerae, Clostridium difficile, Clostridium botulinum, Escherichia coli, Shigella boydii, Shigella dysenteriae, Shigella flexneri, Shigella sonnei, Salmonella enterica, Salmonella bognori, Ascaris lumbricoides, Giardia lamblia, Entamoeba histolytica,* poliovirus, rotavirus, Adenovirus, Hepatitis A and human immunodeficiency virus.

5. The method of claim 1, wherein the composition comprises a recombinant bacterium comprising a nucleic acid encoding the ATP-hydrolysing enzyme.

6. The method of claim 5, wherein the recombinant bacterium further comprises a nucleic acid encoding the immunogen.

7. The method of claim 5, wherein the recombinant bacterium is *Escherichia coli* or attenuated *Salmonella enterica*.

8. The method of claim 1, wherein the composition comprises a bacteriophage comprising a nucleic acid encoding the ATP-hydrolyzing enzyme.

9. The method of claim 8, wherein the bacteriophage further comprises a nucleic acid encoding the immunogen.

10. The method of claim 1, wherein the composition comprises a viral vector comprising a nucleic acid encoding the ATP-hydrolyzing enzyme.

11. The method of claim 10, wherein the viral vector further comprises a nucleic acid encoding the immunogen.

12. The method of claim 1, wherein the IgA immune response and/or the IgG immune response is a mucosal response.

13. The method of claim 1, wherein the IgA immune response and/or the IgG immune response is in the gut.

14. The method of claim 1, wherein the composition is formulated for administration in a nanocapsule.

* * * * *

SEQUENCE LISTING

```
<160> NUMBER OF SEQ ID NOS: 1

<210> SEQ ID NO 1
<211> LENGTH: 1134
<212> TYPE: DNA
<213> ORGANISM: Shigella flexneri

<400> SEQUENCE: 1
tcacaaatca tcataatcaa gagacaaaac gatacgaaaa aataagataa aaaacatcgt      60
tcttttacca cattattttc cgtgaatatg aaaaataatg ttattacttt aatataagac     120 tatttttgt ttttccatca ctctgttcaa attttccgc atgacttgtg ttttttgtaa      180
tacagctcgt tttttacagc tgaccaaaat catcaattaa ttatgctaag gaaataaatt     240
atgaaaacca aaaactttct tcttttttgt attgctacaa atatgatttt tatcccctca     300
gcaaatgctc tgaaggcaga aggttttctc actcaacaaa cttcaccaga cagtttgtca     360
atacttccgc cgcctccggc agagaattca gtagtatttc aggctgacaa agctcattat     420
gaattcggcc gctcgctccg ggatgctaat cgtgtacgtc tcgctagcga agatgcatac     480
tacgagaatt ttggtcttgc attttcagat gcttatggca tggatatttc aagggaaaat     540
accccaatct tatatcagtt gttaacacaa gtactacagg atagccatga ttacgccgtg     600
cgtaacgcca aagaatatta taaagagtt cgtccattcg ttatttataa agacgcaacc     660
```

-continued

```
tgtacacctg ataaagatga gaaaatggct atcactggct cttatccctc tggtcatgca      720
tcctttggtt gggcagtagc actgatactt gcggagatta atcctcaacg taaagcggaa      780
atacttcgac gtggatatga gtttggagaa agtcgggtca tctgcggtgc gcattggcaa      840
agcgatgtag aggctgggcg tttaatggga gcatcggttg ttgcagtact tcataataca      900
cctgaattta ccaaaagcct tagcgaagcc aaaaaagagt ttgaagaatt aaatactcct      960
accaatgaac tgaccccata aagctggaca gcctgtatca ggctatggag ggcccataga     1020
caaatctacc ctatatgagc ataggaggag tctatgggca caccacgttt taccccctgaa     1080 tttaagggat tactggaaag gctgggacat atcctccggc agaagcagaa aaag           1134
```